(12) United States Patent
Schnoor et al.

(10) Patent No.: US 7,214,509 B2
(45) Date of Patent: May 8, 2007

(54) METHODS AND COMPOSITIONS FOR DEGRADATION OF NITROAROMATIC AND NITRAMINE POLLUTANTS

(75) Inventors: Jerald L. Schnoor, Iowa City, IA (US); Beniot Van Aken, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 355 days.

(21) Appl. No.: 10/873,659

(22) Filed: Jun. 22, 2004

(65) Prior Publication Data

US 2005/0054030 A1 Mar. 10, 2005

Related U.S. Application Data

(60) Provisional application No. 60/483,736, filed on Jun. 30, 2003.

(51) Int. Cl.
*C12N 1/20* (2006.01)
*C12Q 1/12* (2006.01)
*C12P 39/00* (2006.01)
*A62D 3/02* (2006.01)
*B09B 3/00* (2006.01)

(52) U.S. Cl. ............... 435/42; 435/37; 435/252.1; 435/253.6; 435/262.5; 435/975

(58) Field of Classification Search .......... 435/37, 435/42, 252.1, 253.6, 262.5, 975
See application file for complete search history.

(56) References Cited

U.S. PATENT DOCUMENTS 5,543,324 A 8/1996 Rajan et al. ............ 435/252.4
6,132,985 A * 10/2000 Pierce ........................ 435/29

OTHER PUBLICATIONS

Lidstrom, et al., "Plants in the Pink: Cytokinin production by *Methylobacterium*", Journal of Bacteriology (2002), V. 184, p. 1818.
Trotsenko, et al., "Aerobic methylotrophic bacteria as phytosymbionts", Microbiology (2001), V. 70, No. 6, pp. 623-632.
Pirtilla, et al., "Detection of intracellular bacteria in the buds of scotch pine (*Pinus sylvestris* L.) by in situ hybridization", Applied and Environmental Microbiology (2000), V. 66, pp. 3073-3077.
Hawari, et al., "Microbial degradation of explosives: Biotransformation versus mineralization", Applied Microbiology and Biotechnology (2000), V. 54, pp. 605-618.
Rosser, et al., "Microbial transformation of explosives", Advances in Applied Microbiology (2001), V. 49, pp. 1-35.
Gorontzy, et al., "Microbial degradation of explosives and related compounds", Critical Reviews in Microbiology (1994), V. 20, pp. 265-284.
Holland, et al., "PPFMs and other covert contaminats: Is there more to plant physiology than just plant?", Annual Review of Plant Mol. Biol. (1994), V. 45, pp. 197-209.
Schnoor, et al., "Phytoremediation of organic and nutrient contaminants", Environmental Science and Technology (1995), V. 29, pp. 318A-323A.
Van Aken, "Biodegradation of nitro-substituted explosives by white-rot fungi: A mechanistical approach", Advances in Applied Microbiology (2001), V. 48, pp. 1-77.
Nishino, et al., "Strategies for aerobic degradation of nitroaromatic compounds by bacteria: Process discovery to field application", p. 7-61. In J.C. Spain, J.B. Hughes, and H.J. Knackmuss (ed.), Biodegradation of Nitroaromatic Compounds and Explosives (2000), Lewis Publishers, New York, NY.
Lenke, et al., "Perspectives of bioelimination of polyaromatic compounds", p. 91-126. In J.C. Spain, J.B. Hughes, and H.J. Knackniuss (ed.), Biodegradation of Nitroaromatic Compounds and Explosives (2000), Lewis Publishers, New York, NY.
Green, P. N., "The genus *Methylobacterium*", p. 2342-2349. In A. Balows, H.G. Truper, M. Dworkin, W. Harder, and K.H. Schleifer (ed.), The Prokaryotes (1992), 2nd ed. Springer-Verlag, Berlin, Germany.
The International Search Report (PCT/US04/20071), Apr. 12, 2005.

* cited by examiner

*Primary Examiner*—Herbert J. Lilling
(74) *Attorney, Agent, or Firm*—Kathleen M. Williams; Mark J. FitzGerald; Edwards Angell Palmer & Dodge, LLP

(57) ABSTRACT

The invention relates to novel *Methylobacterium* species that are capable of degrading nitroaromatic and nitramine compounds. Compositions, kits and methods of using the *Methylobacterium* species for the degradation of nitroaromatic and nitramine pollutants are provided. More specifically, compositions and methods for the degradation or bioremediation of nitroaromatic and nitramine explosives and explosive residues are provided.

34 Claims, 14 Drawing Sheets

Figure 1
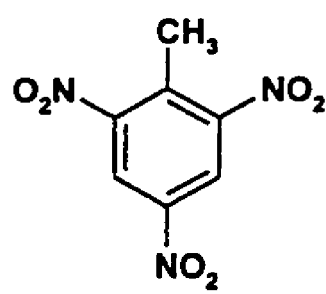
TNT
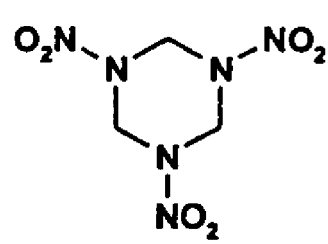
RDX
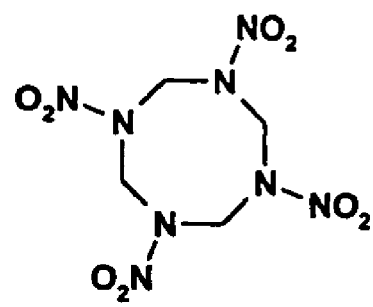
HMX

Figure 4
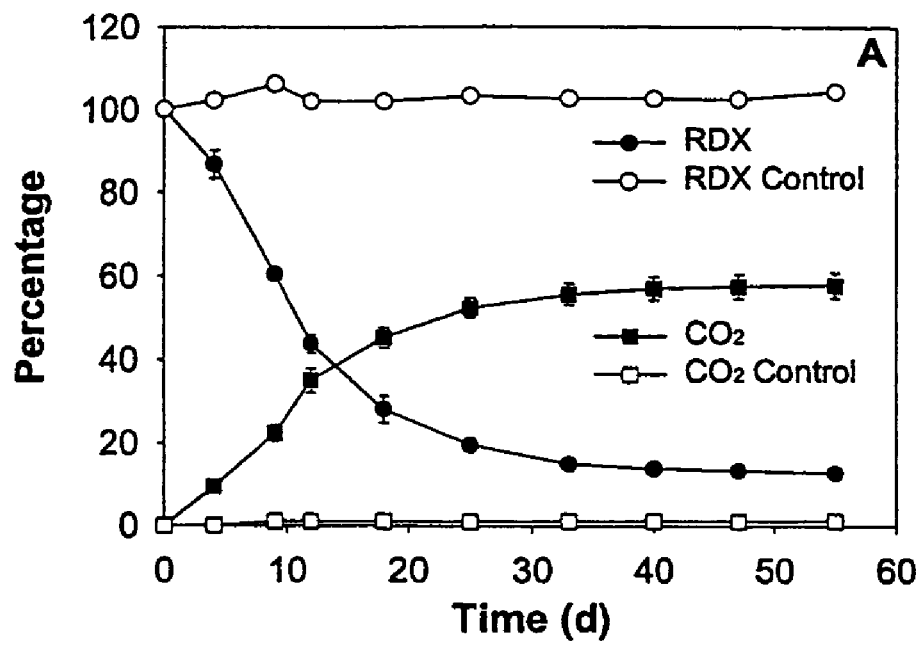
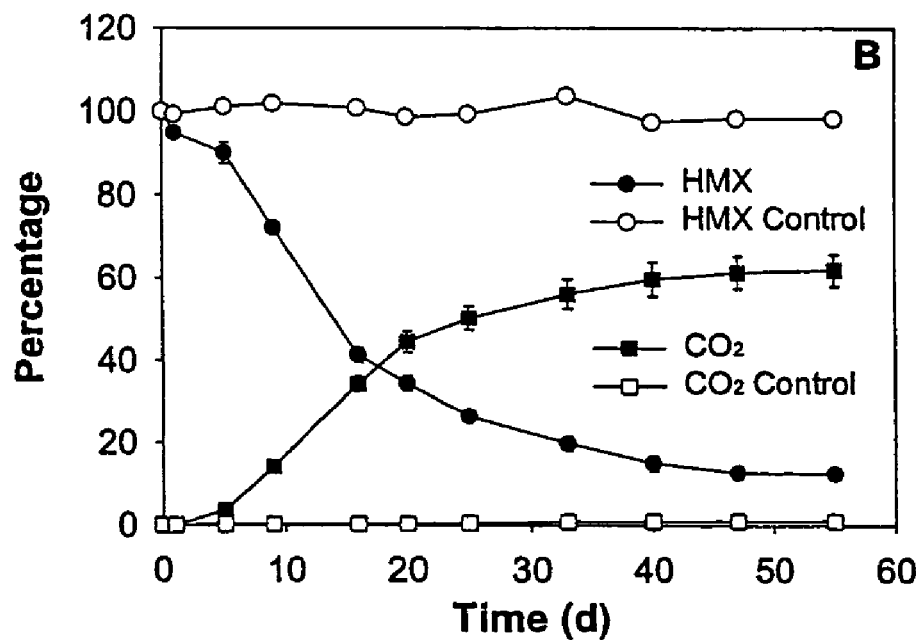

(SEQ ID NO: 1)

```
agggtttgat cctggctcag agcgaacgct ggcggcaggc ttaacacatg caagtcgaac   61
gggcttcttc ggaagtcagt ggcagacggg tgagtaacac gtgggaacgt gcccttcggt  121
tcggaataac tcagggaaac ttgagctaat accggatacg cccttacggg gaaaggttta  181
ctgccgaagg atcggcccgc gtctgattag cttgttggtg gggtaacggc ctaccaaggc  241
gacgatcagt agctggtctg agaggatgat cagccacact gggactgaga cacggcccag  301
actcctacgg gaggcagcag tggggaatat tggacaatgg gcgcaagcct gatccagcca  361
tgccgcgtga gtgatgaagg ccttaggggtt gtaaagctct tttgtccggg acgataatga  421
cggtaccgga agaataagcc ccggctaact tcgtgccagc agccgcggta atacgaaggg  481
ggctagcgtt gctcggaatc actgggcgta aagggcgcgt aggcggccga ttaagtcggg  541
ggtgaaagcc tgtggctcaa ccacagaatt gccttcgata ctggttggct tgagaccgga  601
agaggacagc ggaactgcga gtgtagaggt gaaattcgta gatattcgca agaacaccag  661
tggcgaaggc ggctgtctgg tccggttctg acgctgaggc gcgaaagcgt ggggagcaaa  721
caggattaga taccctggta gtccacgccg taaacgatga atgccagccg ttggcctgct  781
tgcaggtcag tggcgccgct aacgcattaa gcattccgcc tggggagtac ggtcgcaaga  841
ttaaaactca aaggaattga cggggggcccg cacaagcggt ggagcatgtg gtttaattcg  901
aagcaacacg cagaaccttaa ccatcccttg acatggcatg ttacctcgag agatcgggga  961
tcctcttcgg aggcgtgcac acaggtgctg catggctgtc gtcagctcgt gtcgtgagat 1021
gttgggttaa gtcccgcaac gagcgcaacc cacgtcctta gttgccatca ttcagttggg 1081
cactctaggg agactgccgg tgataagccg cgaggaaggt gtggatgacg tcaagtcctc 1141
atggcccttta cgggatgggc tacacacgtg ctacaatggc ggtgacagtg ggacgcgaaa 1201
ccgcgaggtt gagcaaatcc ccaaaagccg tctcagttcg gattgcactc tgcaactcgg 1261
gtgcatgaag gcggaatcgc tagtaatcgt ggatcagcac gccacggtga atacgttccc 1321
gggccttgta cacaccgccc gtcaccat gggagttggt cttacccgac ggcgctgcgc 1381
caaccgcaag ggggcaggcg accacggtag ggtcagcgac tggggtgaag tcgtaacaag 1441
gtagccgtag gggaacctgc ggctggatca cctcctttct aaggatgttt cttttgggag 1501
tttggctccg gccgatctgc tactcgagac gtcattggat acatgaagcc cagtcaggcc 1561
ttcgattggc gggacctgga gaggccgccc tcgtttctct ttctcatccg gataagcggg 1621
atcgctggac gcggcgttgc gtgatgcaac ggctgtcgat cgggcgaccg gctggggcct 1681
gtagctcagg tggttagagc gcaccctga taagggtgag gtcggacgtt cgagtcgtcc 1741
caggcccacc atgatcaggg gacgtagctc agctgggaga gcagttgctt tgcaagcatc 1801
aggtcgtcgg ttcgatcccg tccgtctcca ccagcgcttc ttcgtgaggc gcggtcgtat 1861
ccggagagag agtgcaagtt tgcccttgtg agtgctgagc gcgcaggcg gcattgatat 1921
cgaacatcgt gaagagggaa tgtggccgca ggttccgcga aagcgggtcg cctgttgcag 1981
gtcatgttcg gcaagcatgt gatgcgggtt ccgagaggag cctgcatcac tggtctttat 2041
cgtgaccgtg gctgggtgat cggcagcagc ttagctgctg cggatcacac cggacatcga 2101
tcatgagagc gatcaagtgc cttaagcaa ttcggtggat gccttggcgc tgagaggcga 2161
tgaaggacgt ggtacgctgc gataagcctt ggggagctgc aacgagctt tgatccaggg 2221
atttccgaat ggggcaaccc ggaatcgaat tcccgcggcc gccatggcgg ccggga
```

Nucleotides 1-1477, 16S ribosomal RNA gene;

Nucleotides 1478-2110, 16S-23S Intergenic Spacer;

Nucleotides 2111-2276, 23S rRNA gene

Figure 8

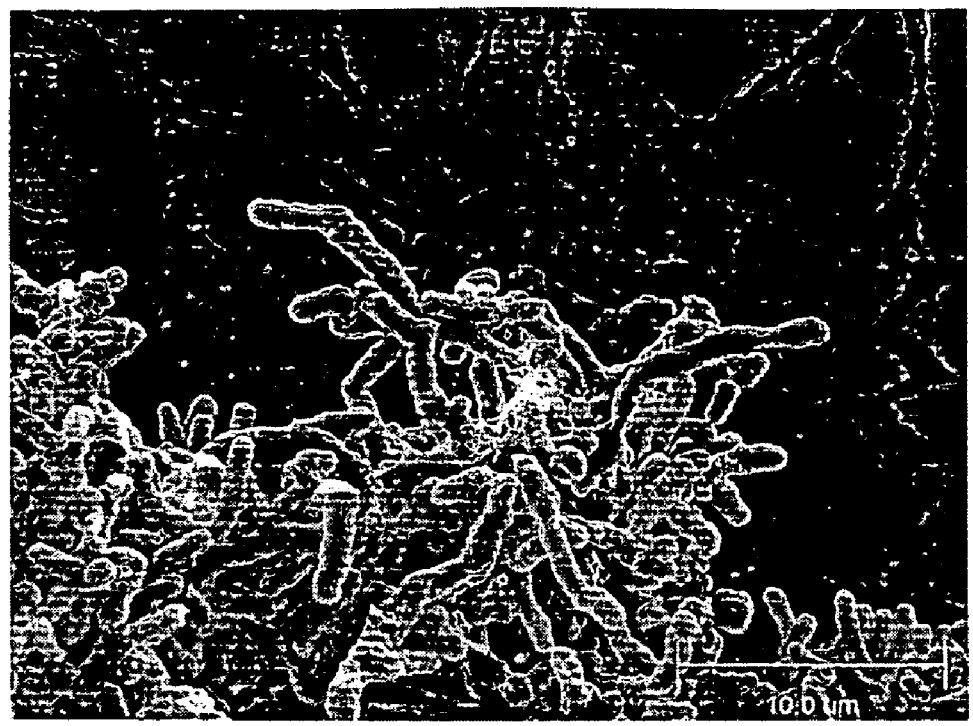
Figure 12

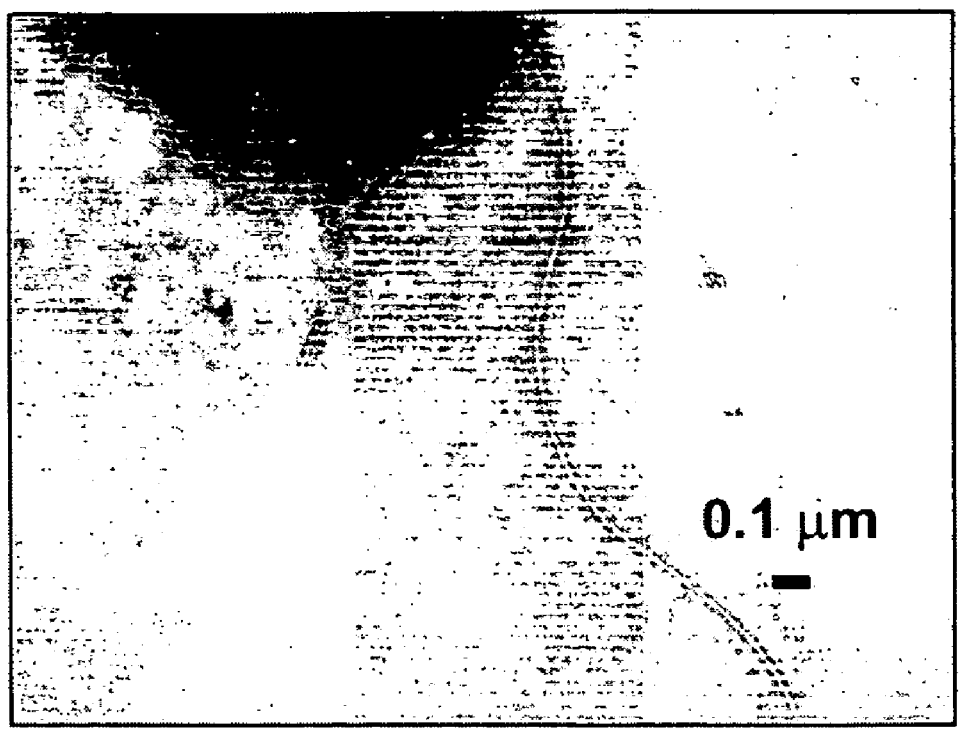
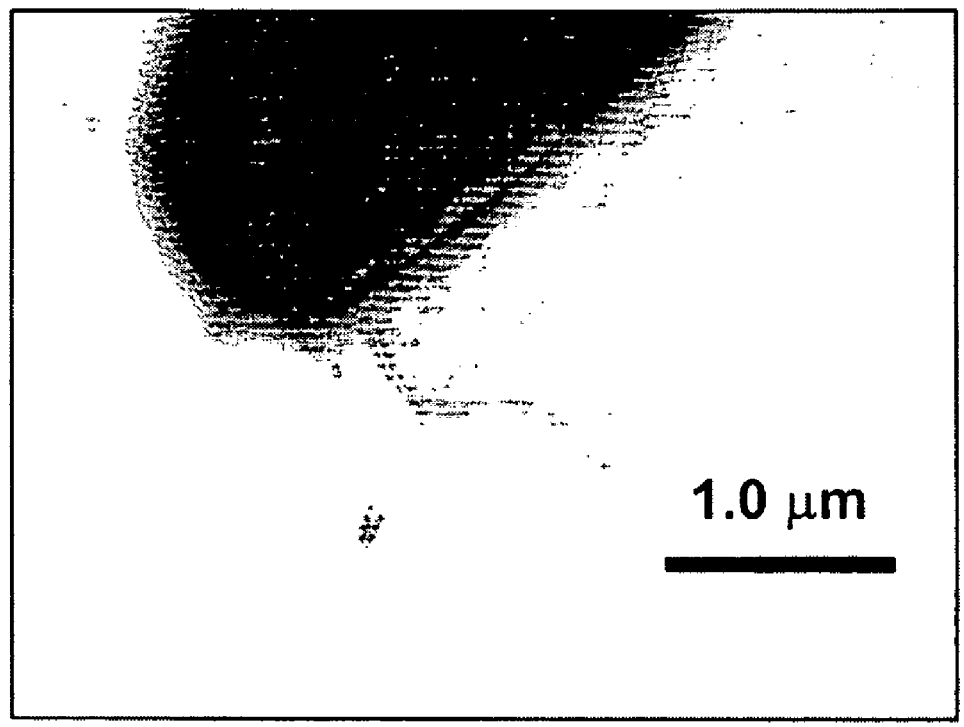
Figure 13

METHODS AND COMPOSITIONS FOR DEGRADATION OF NITROAROMATIC AND NITRAMINE POLLUTANTS

RELATED APPLICATIONS

This application claims the priority of U.S. provisional patent application No. 60/483,736, filed Jun. 30, 2003, the entirety of which is incorporated herein by reference.

BACKGROUND OF THE INVENTION

Nitroaromatic and nitramine compounds comprise a class of pollutants known to have both toxic and carcinogenic properties. Nitroaromatic and nitramine pollutants are frequently generated in the production of explosives, such as TNT (2,4,6-trinotrotoluene), RDX (Royal demolition explosive; hexahydro-1,3,5-trinitro-1,3,5-triazine) and HMX (High melting point explosive; octahydro-1,3,5,7-tetranitro-1,3,5,7-tetrazocine) (see FIG. 1). In particular, due to their low solubility, large quantities of water used in the production of explosives tend to become contaminated during their production, leading to wastewater disposal problems.

First synthesized in 1863, TNT was used in the dye industry before becoming in the 20th century the main conventional explosive used worldwide. However, because of a higher stability and detonation power, nitramines HMX and RDX are at the present time the most widespread conventional explosives. Manufacture of nitro-substituted explosives, testing and firing ranges, and destruction of ammunition stocks have generated toxic wastes leading to large-scale contamination of soils and groundwater (44). Seven nitro-substituted explosives, including TNT and RDX, have been listed as priority pollutants by the U.S. Environmental Protection Agency (EPA) (25). RDX, formerly used as a rat poison, is in addition considered as possible carcinogen by the EPA (2, 28). HMX has been listed as an EPA contaminant of concern (48). A lifetime health advisory of 2 $\mu L^{-1}$ of TNT in drinking water and a water-quality limit of 105 $\mu g\ L^{-1}$ of RDX have been recommended (7, 37). Physicochemical properties, biodegradation, and toxicity of nitro-substituted explosives have been extensively reviewed in the literature (12, 18, 38, 43, 45, 53).

The toxicity of TNT has been reported since the First World War among English ammunition workers. From laboratory studies TNT, RDX, and HMX have been found to be toxic for most classes of organisms, including bacteria (46, 57), algae (46, 57), plants (35), earthworms (36), aquatic invertebrates (46, 48), animals (22, 42), mammals (28, 48), and humans (3, 22).

Traditional treatments of toxic ammunition wastes (i.e. open burning/open detonation (OB/OD), adsorption onto activated carbon, photooxidation (UV/$O_3$), etc.) are costly, damaging for the environment, and in most cases practically infeasible.

Biotransformation of energetic pollutants TNT, RDX, and HMX have been reported for different classes of organisms, including bacteria, fingi, and plants (12, 18, 29, 33, 38, 41, 53). Metabolism of TNT typically involves a sequential reduction of the nitro groups to form toxic aromatic amino derivatives, which are poorly further transformed (29, 33). Except with white-rot fungi, that secrete powerful ligninolytic peroxidases (8, 54), no significant mineralization has been detected in biological systems (29). In contrast to TNT, whose limiting degradation step is the aromatic ring fission, as soon as nitramines RDX and HMX undergo a change of the molecular structure, the ring collapses to generate small aliphatic metabolites (17, 53). While other decomposition mechanisms have been reported (i.e. concerted decomposition, bimolecular elimination, or hydrolysis (17)), biotransformation of RDX and HMX frequently involves an initial reduction of the nitro groups to form nitroso and hydroxylamino derivatives (31). The latter decompose to unstable aliphatic nitramines, eventually converted into $N_2O$ and $CO_2$ (17,18). Due to different conformations, HMX (crown-type) is chemically more stable and therefore less amenable to biodegradation than RDX (chair-type) (17).

Bacteria of the genus *Methylobacterium* are strictly aerobic, facultative methylotrophic, Gram-negative, rod-shaped bacteria that are able to grow on one-carbon compounds, i.e. methanol or methyamine (13, 30, 51). Members of the genus *Methylobacterium*, which belongs to the α-2 subclass of *Proteobacteria*, are distributed in a wide diversity of natural and human-made habitats, including soils, air, dust, fresh water, aquatic sediments, marine environments, water supplies, bathrooms, and masonry (19, 51). Some species have been described as opportunistic human pathogens (51). In addition, methylotrophic bacteria colonize the roots and the leaves of terrestrial and aquatic plant species (21, 34, 51). These bacteria are often red to pink due to the presence of carotenoids and referred as pink-pigmented facultative methylotrophs (PPFMs). *Methylobacterium* bacteria are highly resistant to dehydration, freezing, chlorination, UV light, ionizing radiations, and elevated temperatures (51).

SUMMARY OF THE INVENTION

The invention provides novel strains of *Methylobacterium* species and methods for using them and other species of the genus *Methylobacterium*. These bacteria are shown herein to have the capacity to degrade nitroaromatic and nitramine compounds, including, for example the explosives TNT, HMX and RDX and their derivatives. The capacity of the newly identified bacteria to degrade such nitroaromatic and nitramine compounds provides new methods for the decontamination of environmental materials containing such compounds. Degradation of nitroaromatic and nitramine compounds is generally accomplished by contacting the bacteria with the compounds. The contacting can be performed in the environment, or in isolation using materials, e.g., soil, sediment or wastewater removed from the environment.

The invention also provides compositions, preparations and kits comprising the new *Methylobacterium* species and methods of making them.

In one aspect, the invention encompasses a method for degrading a nitroaromatic or nitramine compound (or compounds), the method comprising contacting the compound with an isolated bacterium having all identifying characteristics of the *Methylobacterium* species, strain BJ001 having ATCC Accession No. PTA-5125 and NCIMB Accession No. 13946, whereby the concentration of the compound is reduced and one or more degradation products is produced.

In one embodiment, the compound is an explosive or high energy compound.

In another embodiment, the compound is selected from the group consisting of TNT, RDX and HMX.

In another embodiment, the degradation products of the degrading have reduced toxicity relative to the toxicity of the nitroaromatic or nitramine compound or compounds degraded.

In another embodiment, the compound is substantially mineralized to $CO_2$ and $H_2O$ by the method.

In another embodiment, the contacting comprises distributing a composition comprising said bacterium over an area in which one seeks to degrade such a compound or a mixture of such compounds.

In another embodiment, the composition comprising the bacterium is distributed over an area of soil, fresh water or sediment contaminated by such a compound or a mixture of such compounds.

In another embodiment, the contacting comprises combining a composition comprising such a bacterium with soil, water or sediment obtained from a site contaminated with such a compound or a mixture of such compounds.

In another embodiment, the contacting comprises combining a preparation comprising an isolated bacterium having all identifying characteristics of the *Methylobacterium* sp. BJ001 having ATCC Accession No. PTA-5125 and NCIMB Accession No. 13946 with a sample comprising a nitroaromatic or nitramine compound or a mixture of such compounds. In another embodiment, the preparation further comprises one or more additional microorganisms. In another embodiment, the preparation comprises one or more additional species of Methylobacterium. In another embodiment, the sample is a soil sample.

In another embodiment, the preparation further comprises one or more nutrients for the *Methylobacterium*.

In another embodiment, the method comprises the addition of one or more soil amendments to a soil sample. The one or more soil amendments can comprise a material, such as manure, wood chips or sawdust, potato scraps, apple pomace, and corncobs, among others, or any carbon source suitable to support the growth of *Methylobacterium* bacteria. Soil amendment materials can be used in varying proportions, depending upon the composition of the soil to be decontaminated and the type of amendment used, from for example a soil to amendment ratio of 1000:1 (w/w), 500:1, 200:1, 100:1, 50:1, 10:1, 5:1, or even 1:1, 1:2, 1:5 or 1:10.

In another aspect, the invention encompasses a method of identifying a *Methylobacterium* that degrades a nitroaromatic or nitramine compound, the method comprising: contacting tissue from a tree with a sterile preparation of growth medium that supports the growth of *Methylobacterium* species; incubating the preparation of growth medium under conditions that permit the growth of *Methylobacterium* species; isolating a pure culture of a *Methylobacterium* species from the growth medium; and contacting the isolated *Methylobacterium* species with a nitramine or nitroaromatic compound; and determining whether the nitroaromatic or nitramine compound is degraded, wherein degradation of the nitramine or nitroaromatic compound identifies the *Methylobacterium* as a species that degrades a nitroaromatic or nitramine compound.

In one embodiment, the tissue is from a Poplar tree.

In another embodiment, the tissue from a tree is a surface-sterilized tissue explant, tissue grown in tissue culture, or a regenerated plantlet.

In another embodiment, the growth medium comprises LB, NA or modified Jayasuriya's medium.

In another aspect, the invention provides an isolated *Methylobacterium* having the identifying characteristics of the *Methylobacterium* sp. BJ001 having ATCC Accession No. PTA-5125 and NCIMB Accession No. 13946.

In another aspect, the invention provides an isolated *Methylobacterium* which is the *Methylobacterium* sp. BJ001 having ATCC Accession No. PTA-5125 and NCIMB Accession No. 13946.

In another aspect, the invention provides a method of preparing *Methylobacterium* sp. BJ001 comprising: inoculating a sterile preparation of growth medium that supports the growth of *Methylobacterium* species with a cell of *Methylobacterium* sp. BJ001 having the identifying characteristics of ATCC Accession No. PTA-5125 and NCIMB Accession No. 13946; and incubating the preparation of growth medium to produce a preparation of the *Methylobacterium* sp. BJ001.

In one embodiment, the growth medium comprises Luria Bertani (LB) medium, Nutrient Agar (NA) or modified Jayasuriya's medium.

In another aspect, the invention encompasses a composition comprising an isolated *Methylobacterium* having all identifying characteristics of the *Methylobacterium* sp. BJ001 having ATCC Accession No. PTA-5125 and NCIMB Accession No. 13946, and a high energy compound, including, for example, a nitramine or nitroaromatic explosive.

In one embodiment, the nitramine or nitroaromatic explosive is one or more of TNT, RDX and HMX.

In another embodiment, the composition further comprises one or more additional microorganisms. In another embodiment, one or more of such additional microorganisms belong to the genus *Methylobacterium*.

In another embodiment, the composition further comprises one or more nutrients for the *Methylobacterium*.

In another aspect, a preparation of *Methylobacterium* sp. BJ001, having ATCC Accession No. PTA-5125 and NCIMB Accession No. 13946 is provided, the preparation having a concentration of at least 1% (v/v) of the *Methylobacterium* inoculum. In one embodiment, the preparation has a cell concentration of 1% to about 95% by volume.

In another aspect, there is provided a composition comprising an aqueous slurry of solid material comprising a nitroaromatic or nitramine compound, and a *Methylobacterium* species having the identifying characteristics of *Methylobacterium* sp. BJ001 having ATCC Accession No. PTA-5125 and NCIMB Accession No. 13946, the aqueous slurry being 30% solid material (w/w).

In one embodiment, the *Methylobacterium* species is present at a density of $10^9$ cells/ml or greater.

In another embodiment, the composition has a pH in the range of pH 3.0 to pH 11.0. In another embodiment, the pH is in the range of pH 6.0 to pH 8.0. In another embodiment, the composition is at a temperature of 4° C. to 41° C. In another embodiment, the composition of is at a temperature of 15° C. to 37° C.

In another embodiment, the composition is at an oxygen saturation of 5% to 100%. In another embodiment, the composition is at an oxygen saturation of 20% to 100%.

In another aspect, a preparation is provided comprising viable, dried *Methylobacterium* sp. BJ001 having ATCC Accession No. PTA-5125 and NCIMB Accession No. 13946.

In one embodiment, the preparation further comprises an additional microbial species. In one embodiment, the additional microbial species comprises a bacterial species belonging to the genus *Methylobacterium*.

In another embodiment, the preparation further comprises one or more nutrients for the *Methylobacterium*. Such nutrient(s) aid the bacterium in growth upon recovery from the dried state. Such nutrients include, as non-limiting examples, methanol, ethanol, formate, succinate and fructose.

In another aspect, there is provided a *Methylobacterium* isolated by the steps of: contacting a Poplar tissue with a sterile preparation of growth medium that supports the growth of *Methylobacterium* species; and isolating a single red or pink-colored bacterial colony from said preparation.

In one embodiment, the growth medium that supports the growth of *Methylobacterium* species is LB medium.

In another embodiment, the *Methylobacterium* degrades a nitroaromatic or nitramine compound.

In another embodiment, the *Methylobacterium* degrades a high energy compound.

In another embodiment, the *Methylobacterium* degrades TNT, RDX or HMX.

In another embodiment, the Poplar tissue comprises a tissue explant from a Poplar tree. In another embodiment, the Poplar tree is *Populus deltoides×nigra* DN34.

In another embodiment, the Poplar tissue is from tissue culture.

In another embodiment, the Poplar tissue is tissue from a regenerated plantlet.

In another aspect, there is provided a kit for the degradation of a nitramine or nitroaromatic compound, the kit comprising a *Methylobacterium* having the identifying characteristics of the species having ATCC Accession No. PTA-5125 and NCIMB Accession No. 13946.

Definitions:

As used herein, the term "degrading" refers to the conversion of a nitroaromatic or nitramine compound to a form that has reduced toxicity compared to the starting compound. "Degrading" requires the cleavage of one or more chemical bonds in a nitroaromatic or nitramine target compound. A "degradation product" is a composition resulting from degrading a nitramine or nitroaromatic compound. The term "degradation product" encompasses products ranging from a compound differing from a starting nitramine or nitroaromatic compound by one or more chemical bonds, to a fully mineralized degradation product of such nitramine or nitroaromatic compound. The degradation of nitroaromatic and nitramine compounds can be measured by HPLC and radioactive tracer assays as described herein. Nutrients include, for example, carbon sources (e.g., carbohydrates, methanol, succinate, etc.) minerals, vitamins, nitrogen sources, and phosphorus sources.

As used herein, the term "reduced toxicity" means that the product or products of a degradation process are less toxic to a test organism under conditions in which the compound degraded is toxic to that organism. Toxicity is commonly expressed in terms of the LD50, the dose of a toxin at which 50% of a test organism is killed. Generally, toxicity of a compound is "reduced" relative to a parent compound if the $LD_{50}$ of the compound is at least 10% higher than the $LD_{50}$ of the parent compound.

As used herein, the term "reduced concentration" when used in reference to a nitroaromatic or nitramine compound means that the concentration of the compound is reduced by at least 1%, and preferably more, e.g., at least 5%, 10%, 20% or more, up to and including 100% (no compound remaining), relative to the concentration prior to the combination of a sample with a *Methylobacterium* species as described herein.

As used herein, the term "explosive" refers to a nitroaromatic or nitramine compound that explodes upon application of heat or shock. The term "high energy compound" also refers to a nitroaromatic or nitramine compound that explodes upon application of heat or shock.

As used herein, the term "nitroaromatic" refers to an aromatic hydrocarbon compound containing one or more nitro groups in place of a hydrogen atom or atoms.

As used herein, the term "nitramine" refers to a compound comprising the chemical structure $R_1R_2N$—$NO_2$ where $R_1$ and $R_2$ can be any substituent. Preferred nitramines are heterocyclic nitramines, such as RDX and HMX.

As used herein, the term "isolated," when used in reference to a *Methylobacterium* strain, means that the bacterium is not physically associated with a tissue of a tree of the genus *Populus*. An "isolated" bacterium is preferably, but not necessarily a pure culture of the bacterium.

As used herein, the term "identifying characteristics," when used in reference to *Methylobacterium* sp. BJ001, means the bacterium is a strictly aerobic, facultative methylotrophic, Gram negative rod, and can grow on one-carbon compounds including methanol, methane, formaldehyde, and methylamine. Additional "identifying characteristics" include growth on fructose, acetate, betaine, tartrate, formate, propionate, oxalate, lactate, salicylate, pyruvate, succinate, fumarate, glycerol and ethanol, but lack of growth on saccharaose, arabinose, galactose, glucose, lactose, mannose, xylose, fucose, iso-propanol, n-butanol, inositol, mannitol, sorbitol, aspartate, glutamate, citrate, sebacate, dimethylamine, trimethylamine, chloromethane, dichloromethane, methyl tert-butyl ether, TNT, RDX and HMX. Additional "identifying characteristics" include the presence of the following enzymatic activities: oxidase, catalase, alkaline phosphatase, $C_4$ and $C_8$ esterases, valine arylamidase, α-chymotrypsin, acid phosphatase and naphthol-AS-BI-phosphohydrolase. (Using biochemical assays, strain BJ001 is tested positive for the following enzymatic reactions: Akaline phosphatase (2-naphthyl phosphate), esterase $C_4$ (2-naphtyl butyrate), esterase $C_8$ (2-naphthyl carylate), valine arylamidase (L-valyl-2-naphtyhlamide), α-chymotrypsine (N-glutaryl-phenylalanine-2-naphtylamide), acid phosphatase (2-naphtyl phosphate), and naphtol-AS-BI-phosphohydrolase (naphtol-AS-BI-phosphate or 6-Bromo-2-phosphohydroxy-3-naphthoic acid α-anisidide)). *Methylobacterium* species according to the invention have greater than or equal to 95% 16S ribosomal DNA and 16S-23S IGS DNA sequence similarity to the 16S rDNA and 16S-23S IGS sequence provided in FIG. 8. *Methylobacterium* species according to the invention have as an "identifying characteristic" the ability to metabolize nitramine and nitroaromatic substrates including TNT, RDX and HMX, and the ability to mineralize RDX and HMX. Additional "identifying characteristics" include doubling time. A doubling time of 9.7 h is determined for *Methylobacterium* sp. BJ001 growing on LB medium supplemented with fructose (0.5% w/v), an optimum carbon source supporting the growth of BJ001. No growth is observed on saccharose, arabinose, galactose, iso-propanol, n-butanol, chloromethane, dichloromethane, TNT, RDX, or HMX.

As used herein, the term "mineralized" means that a compound has been completely transformed to $CO_2$, $H_2O$, and a mineral form of nitrogen, i.e., $N_2$, $NO_x$ or $NH_4$. The term "substantially mineralized" means that at least 10%, and preferably more (e.g., 20%, 30%, 40%, 50%, 60%, 70%, 80%, 90%, 95% or more, up to and including 100%) of a given amount of a nitroaromatic or nitramine compound (e.g., a nitroaromatic or nitramine explosive) is mineralized.

As used herein, the term "distributing" means applying a composition comprising a bacterium to an area of contaminated soil or water. The composition is preferably applied in a substantially uniform manner, although uniformity is not absolutely required. Distribution can include, for example, spraying or sowing a composition in liquid, solid or semi-solid form. Distribution can also be accomplished by mixing an inoculum of bacterium-containing composition into a soil sample removed from a contaminated site.

As used herein, the term "environment" refers to an area contaminated with a nitramine or nitroaromatic compound, the area being a body of water (e.g., stream, lake or pond, man-made or natural) and/or the ground or sediment under the water, or a piece of land (e.g., a field, landfill, industrial manufacturing or storage site).

As used herein, the phrase "growth medium that supports the growth of *Methylobacterium* species" refers to a sterile preparation which supports the growth of *Methylobacterium* sp. BJ001. Non-limiting examples include LB medium, NA medium, modified Jayasuriya's medium, and DSMZ (Deutsche Sammlung von Mikroorganismen und Zellkulturen, Braunschweig, Germany) *Methylobacterium* Medium 125. One of skill in the art can readily determine whether a given medium preparation supports the growth of *Methylobacterium* sp. BJ001 or other *Methylobacterium* species, e.g., by inoculating the medium with strain BJ001 or other *Methylobacterium* species and incubating it at 28° C., thereafter monitoring bacterial growth by, e.g., $OD_{600}$ or other suitable means.

As used herein, the term "modified Jayasuriya's medium" refers to an aqueous medium in which 1 liter contains 1.74 g of $K_2HPO_4$, 1.38 g $NaH_2PO_4.H_2O$, 0.54 g $Na_2SO_4$, 0.2 g $MgSO_4.7H_2O$, 25 mg $CaCl_2.2H_2O$, 3.5 mg $FeCl_2.4H_2O$, and 2 ml of mineral solution (Wolfe's Trace Mineral Solution, ATCC Catalog No. MD-TMS). The medium has a pH of 7.0. For the growth of *Methylobacterium* sp. BJ001, the modified Jayasuriya's medium is supplemented with 0.5% w/v fructose, 0.2% w/v succinate or 0.5% v/v methanol and 1.2 g/L $NH_4NO_3$.

As used herein, the phrase "conditions that support the growth of *Methylobacterium* species" refers to culture conditions including a growth medium that supports the growth of *Methylobacterium* species as the term is defined herein, pH 3.0 to pH 11.0 (preferably about pH 6.0 to about pH 8.0), temperature of 4° C. to 41° C. (preferably about 15° C. to about 37° C.), and oxygen conventration of 5% to 100% saturation (preferably about 20% to about 100% saturation).

As used herein, the term "tissue explant" refers to living tissue removed from a plant. Tissue explants can come from any living tissue of the plant, e.g., the roots, stem, leaves, etc.

As used herein, the phrase "surface sterilized" means a plant tissue has been treated to kill all bacteria on the outside of the plant tissue. Surface sterilization can be achieved, for example, by successive immersion in 10% v/v bleaching solution (initially 5.25% sodium hypochloride (NaClO)) for 20 min, in 1.0% v/v Iodophor Sanitizer (National Chemicals, Inc., Winona, Minn.) for 5 min, in 70% v/v ethanol for 2 min, followed by rinsing with sterile DI water.

As used herein, the term "regenerated plantlet" refers to a plant grown from a plant cell tissue culture or plant explant by a vegetative way.

As used herein, the term "viable" means that the bacterium is capable of growth and division. Viability is tested by inoculation into medium and incubation under conditions permissive for growth of the bacterium.

As used herein, the term "dried" when referring to a bacterial preparation means a preparation of cells retaining less than 10% residual moisture, preferably, under 5%, even more preferably, less than 3.5–4% residual moisture, most preferably about 2–3% residual moisture. The amount of residual moisture can be evaluated by any method known to those skilled in the art, which include, but are not limited to, i) Karl Fischer Thermal method, ii) Thermogravimetry/Mass Spectometry (TG/MS), iii) Moisture evolution method and Vapor pressure moisture method, iv) gas chromatography, v) Near infared reflectance (NIR) spectroscopy, vi) Gravimetric (loss-on-drying) method, vii) Differential scanning calorimetry (DSC), and viii) Thermally stimulated polarization current (TSPC).

As used herein, the term "nutrient" means an organic or inorganic chemical moiety that is taken up by and promotes the growth or metabolism of *Methylobacterium* sp. BJ001. "Nutrients" as used herein include, for example, carbon sources (e.g., carbohydrates, organic acids, methanol, etc.), minerals, vitamins, nitrogen sources, and phosphorus sources.

As used herein, the term "soil amendment" refers to a composition used to modify nitramine- or nitroaromatic-contaminated soil in a manner that increases the ability of the soil to support the nitroaromatic- or nitramine-degrading activity of a *Methylobacterium* species as described herein (i.e., the amendment increases the nitramine or nitroaromatic degradation activity of a *Methylobacterium* species by at least 5% relative to the same soil without that amendment). Without wishing to be bound by any one mechanism of action, a soil amendment can, for example, effectively dilute the concentration of agents toxic to the bacterium, provide vitamins or nutrients (e.g., carbon source, nitrogen, etc.) to the *Methylobacterium* species, adjust the pH, modify the soil's water-retention ability or increase the ease of or degree of aeration of the soil. Exemplary soil amendments include, for example, sand, manure, wood chips, paper shreddings, sawdust, vegetable scrap products of industrial scale food processing (e.g., apple pomace, potato scraps, corncobs, or other vegetable scraps from industrial food processing operations), vermiculite, straw, rice hulls, peat, alfalfa, and grass.

BRIEF DESCRIPTION OF THE DRAWINGS

FIG. 1 shows chemical structures for TNT, RDX and HMX.

FIGS. 4A and B shows a graphical representation of data for the mineralization of (A) $^{14}C$-RDX (20 mg $L^{-1}$), and (B) $^{14}C$-HMX (2.5 mg $L^{-1}$) by pure cultures of *Methylobacte-* rium sp. BJ001. Radioactivity remaining in solution and release of $^{14}CO_2$ are presented. Experiments were conducted with bacteria cell suspensions and in controls consisting of non-inoculated bioreactors. Radioactivity in solution and release of $^{14}CO_2$ are expressed in percentage of the initial level.

Figure 5:
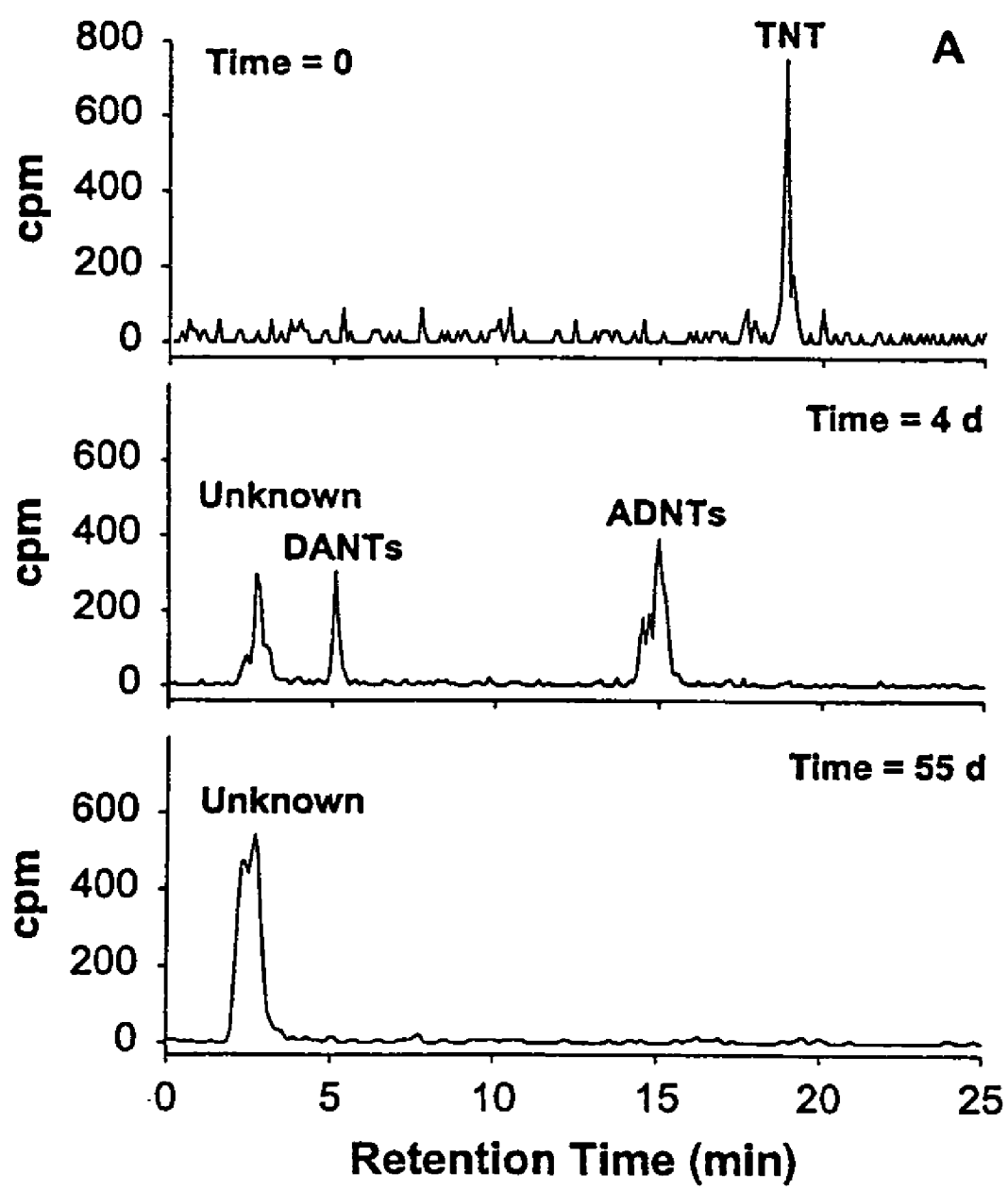

FIGS. 5A and B shows a graphical representation of data for the degradation of (A) $^{14}$C-TNT (25 mg L$^{-1}$) and (B) $^{14}$C-RDX (20 mg L$^{-1}$) by pure cultures of *Methylobacterium* sp. BJ001. Radio-chromatograms obtained from HPLC analysis ($C_{18}$-column) of the liquid medium at time 0, after 4 days, and after 55 days of incubation are presented.

Figure 6:

FIG. 6 shows a photo of a Poplar plantlet (*Populus deltoides×nigra* DN34) regenerated from in vitro tissue cultures and cultivated on semi-solid modified MS medium. Red colonies of *Methylobacterium* sp. BJ001 are well visible.

Figure 7:
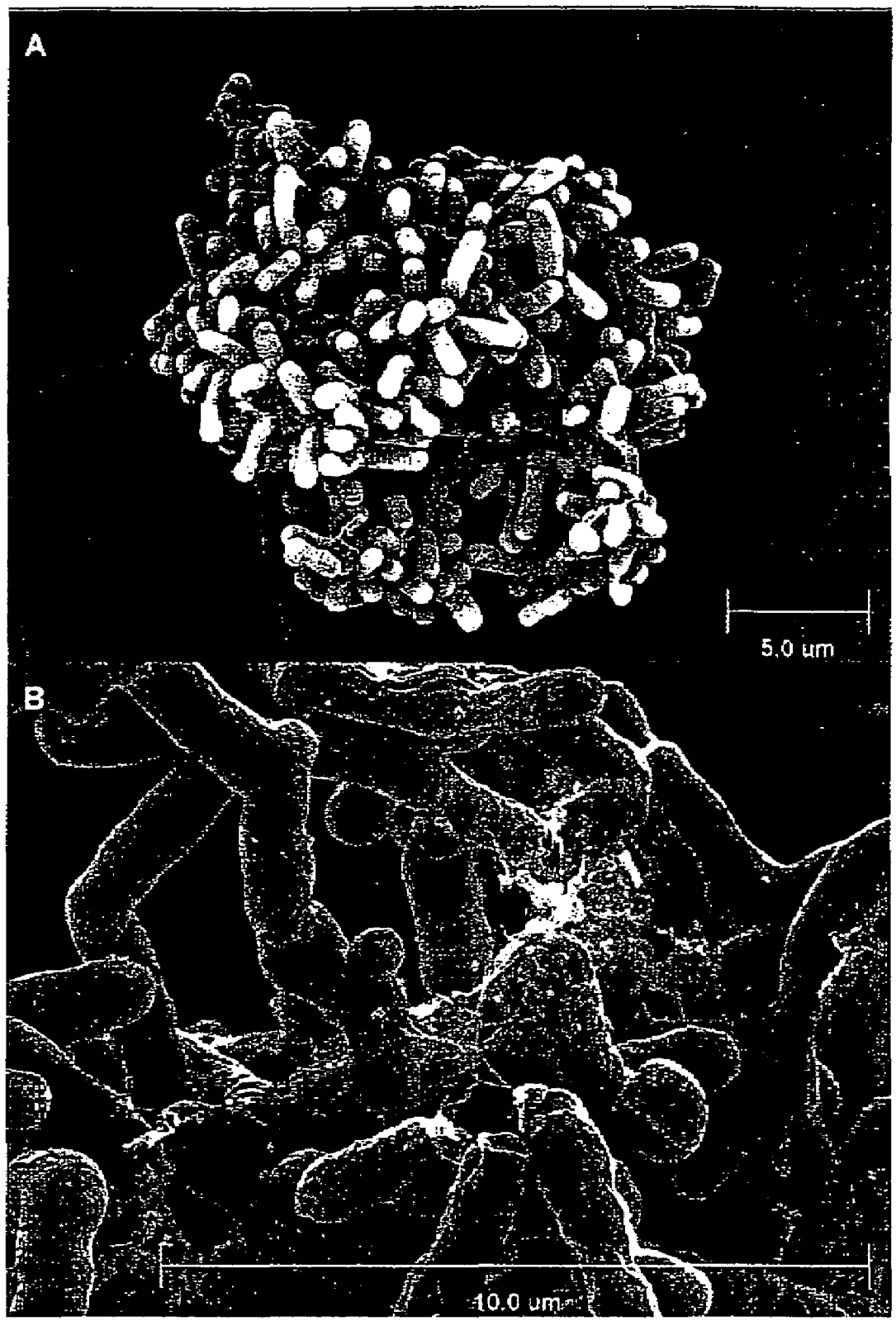

FIGS. 7A and B shows SEM images of *Methylobacterium* sp. BJ001 cultivated (A) on solid LB medium and (B) in liquid LB medium.

FIG. 8 shows the nucleotide sequences of *Methylobacterium* sp. BJ001 16S rRNA gene and the 16S-23S Intergenic Spacer (IGS).

Figure 9:
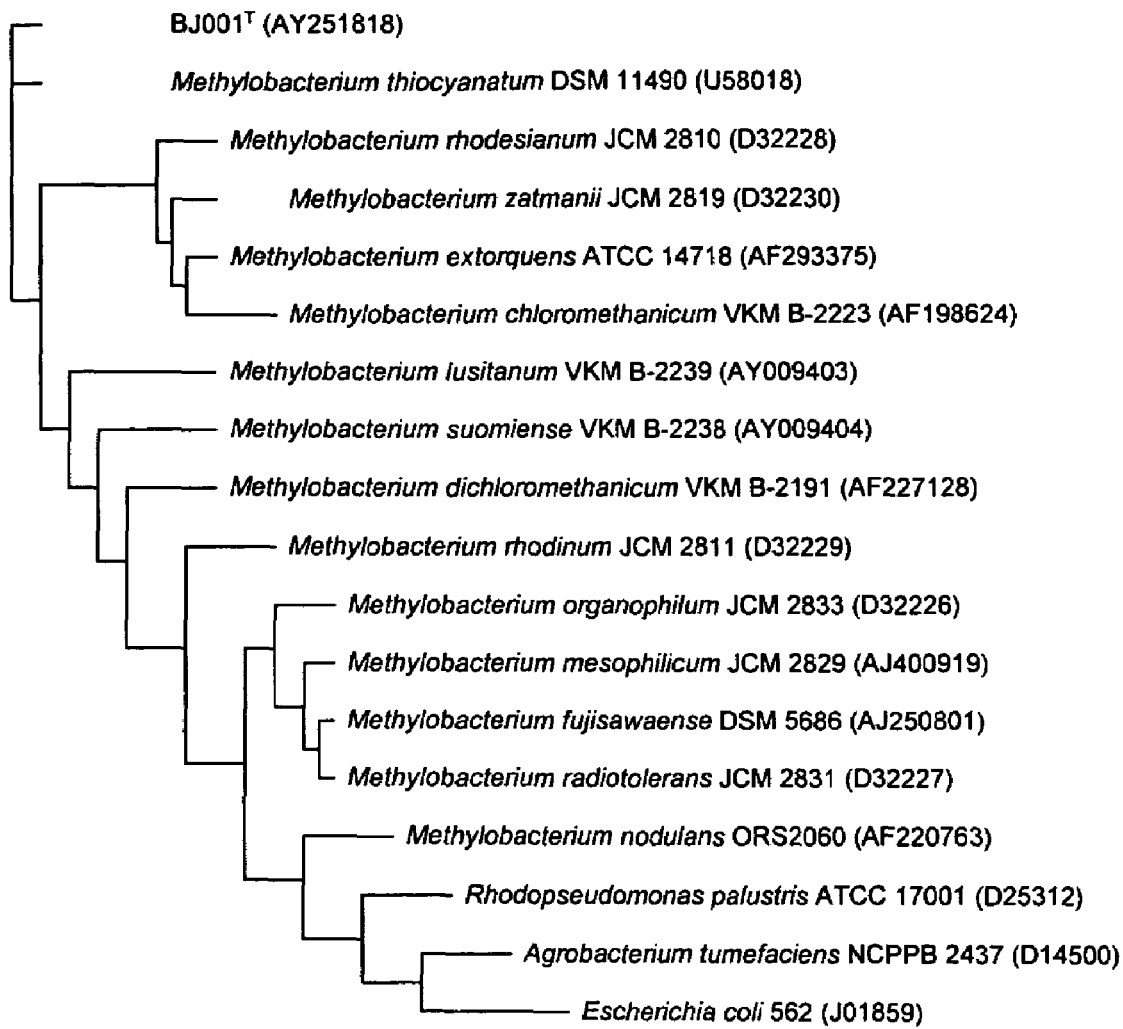

FIG. 9 shows a phylogenetic tree based on the 16S rDNA sequences of members of the genus *Methylobacterium* and further representatives of *Proteoabacteria* showing the location of strain BJ001$^T$ isolated from *Populus deltoids×nigra* DN34. NCBI Genbank accession numbers are provided in parentheses.

Figure 10:

FIG. 10 shows SEM pictures of strain BJ001$^T$ isolted from *Populus deltoides×nigra* DN34.

Figure 11:
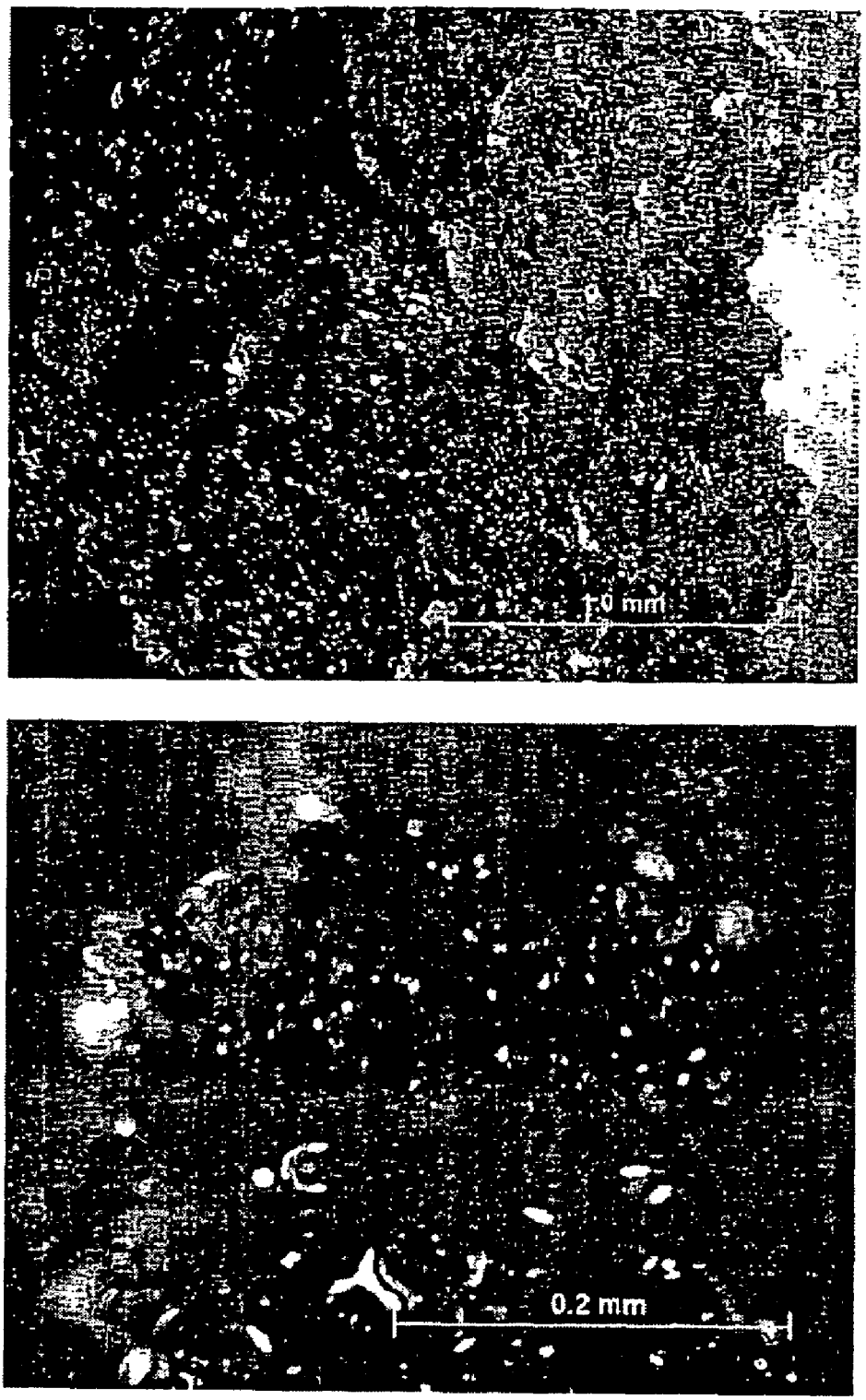

FIG. 11 shows stereoscope microphotographs of poplar tissue cultures (*Populus deltoides×nigra* DN34) containing *Methylobacterium* sp. BJ001$^T$ (Olympus Steroscope SZX-ILLD100; Tokyo, Japan).

FIG. 12 shows scanning electron microscope (SEM) microphotographs of *Methylobacterium* sp BJ001$^T$ (glutaraldehyde-osmium tetroxide fixation, gold-palladium coating; Hitachi S-4000 SEM; Tokyo, Japan).

FIG. 13 shows transmission electron microscope (TEM) microphotographs of *Methylobacterium* sp. BJ001$^T$ (negative staining; Hitachi H-7000 TEM; Tokyo, Japan). A polar (top) and a lateral (bottom) flagella are shown.

DETAILED DESCRIPTION OF THE PREFERRED EMBODIMENTS

*Methylobacteria* as described herein are capable of degrading nitramine and nitroaromatic compounds, which tend to be toxic, to less toxic forms and/or to fully degraded (i.e., mineralized) forms. While not limited to explosive compounds or their partial degradation products or derivatives, nitramine (e.g., heterocyclic nitramine) and nitroaromatic compounds are common contaminants resulting from the production or use of a number of widely used explosive compounds, as described herein above. Such compounds tend to contaminate soil, groundwater and sediments located near sites of production and use of the explosives. By introduction of the novel *Methylobacterium* strain described herein, alone or together with additional microorganisms, including other *Methylobacterium* species, to contaminated soil, groundwater or sediment either still in the environment or in isolation, the species described herein can be used in programs of environmental decontamination.

*Methylobacterium* Species According to the Invention

*Methylobacterium* sp. strain BJ001 as disclosed herein was isolated from tissues of the hybrid poplar *Populus deltoides×nigra* DN34. The strain BJ001 was isolated as described herein below.

A. Bacterial Isolation, Growth, and Maintenance.

A pink-pigmented bacterium was isolated from poplar tissue cultures and plantlets (*Populus deltoides×nigra* DN34) cultivated under axenic conditions. Tissue cultures in liquid medium and intact plantlets (regenerated from in vitro tissues) did not show microbial contamination. However, plant tissues plated on modified MS semi-solid medium frequently turned red, while excised plantlets showed the development of bright-red colonies spreading from the plant material (FIG. 6), suggesting the presence of a bacterium associated with or within poplar tissues. Standard staining procedures and microscopic observations revealed a gram-negative, non-sporulating, rod-shaped bacterium (FIG. 7A), developing a filamentous and branched phenotype in liquid suspension (FIG. 7B). Red or pink-colored single colonies were collected manually from different plant materials, i.e. from surface-sterilized explants, from tissue culture, or from regenerated plantlets, and isolated by streaking on Luria-Bertani (LB) solid medium (2.5% agar) incubated at 28° C. Pure cultures of the isolated bacterium were routinely maintained on the same LB solid medium at 28° C.

For plant tissue cultures and explants, Imperial Carolina hybrid poplar cuttings (*Populus deltoides×nigra* DN34) were obtained from Hramoor Nursery (Manistee, Mich.). Explants from small trees routinely maintained in hydroponic cultures (i.e. 10-mm pieces of young stems and leaves) were surface-sterilized by successive immersion in 10% v/v bleaching solution (initially 5.25% sodium hypochloride (NaClO)) for 20 min, in 1.0% v/v Iodophor Sanitizer (National Chemicals, Inc., Winona, Minn.) for 5 min, in 70% v/v ethanol for 2 min, and then rinsed with sterile DI water (55). Sterilized explants grew on semi-solid medium consisting of Murashige and Skoog (MS) medium (pH 5.8) containing 20 g L$^{-1}$ sucrose, 1.0 g L$^{-1}$ phytagel, 3.0 g L$^{-1}$; phytagar, and 5.0 mg L$^{-1}$ 2,4-dichlorophenoxyacetic acid (2,4-D) and 1.0 mg L$^{-1}$ 6-furfurylaminopurine (kinetin) as growth regulators. The medium was sterilized by autoclaving 25 min at 121° C., 1 atm. After one month of incubation in the dark, actively developing callus material was transferred in sterile liquid MS medium and incubated under agitation (125 rpm) under a 16-h/8-h light/dark photoperiod. After about one month, tissue cultures developed in the form of spherical green cell aggregates (10–20 mm diameter). Tissue cultures were used directly for in vitro experiments as a laboratory plant model and for the regeneration of small plantlets: Green tissues were incubated on root induction medium (semi-solid MS medium supplemented with 203 µg L$^{-1}$ indole-3-butyric acid (IBA) as growth regulator) for 2–4 weeks and then transferred to shoot induction medium (semi-solid MS medium supplemented with 113 µg L$^{-1}$ 6-benzylaminopurine (BA), 110 µg L$^{31}$ $^1$6-(4-hydroxy-3-methylbut-2-enylamino)purine (zeatin), and 5 µg L$^{-1}$ IBA as growth regulators). Plantlets were cultivated under axenic conditions in Magenta boxes with vented lid (Osmotek Lifeline, Rehovot, Israel) under a 16-h/8-h photoperiod.

The isolated *Methylobacterium* sp. BJ001 (also referred to herein as BJ001$^T$, for the "type" strain for this new species) described herein has been deposited under the terms of the Budapest Treaty with both the American Type Culture Collection (Manassas Va.; Accession No. PTA-5125; date of deposit, Apr. 9, 2003) and the National Collections of Industrial and Marine Bacteria (NCIMB; Aberdeen, Scotland, UK; Accession No. 13946; date of deposit, Mar. 13, 2003). The deposits were made for a term of at least thirty (30) years and at least five (5) years after the most recent request for the furnishing of a sample of the deposit is received by the depository, or for the effective term of the patent, whichever is longer, and will be replaced if it becomes non-viable during that period.

Large volumes of Methylobacterium culture can be prepared in LB or other suitable medium. Preparations for application in bioremediation, e.g., dried preparations or microbial mats can be made using methods known in the art. Methylobacterium species are generally quite resistant to desiccation, so standard methods of preparing dried bacteria can be used as known to those skilled in the art or, for example, as disclosed in U.S. Pat. Nos. 6,322,994, 5,733,774 and 5,695,541, each of which is incorporated herein by reference. Dried forms of the bacteria have the advantage of increased storage and transport stability relative to liquid suspensions. U.S. Pat. No. 6,033,559, incorporated herein by reference, describes the preparation of microbial mats for use in bioremediation.

In order to maintain a selective pressure for methylotroph isolation, bacteria were alternatively cultivated in liquid minimal medium supplemented with methanol 0.5% v/v as a carbon source, and ammonium nitrate ($NH_4NO_3$) 1.2 g $L^{-1}$ (i.e. 3.0 mM N) as a nitrogen source. Minimal medium, consisting of modified Jayasuriya's medium, contained in 1 L DI water $K_2HPO_4$, 1.74 g; $NaH_2PO_4.H_2O$, 1.38 g; $Na_2SO_4$, 0.54 ; $MgSO_4.7H_2O$, 0.2 g; $CaCl_2.2H_2O$, 25 mg; $FeCl_2.4H_2O$, 3.5 mg; and mineral solution, 2 ml, at pH 7.0 (16).

C. Morphological, Biochemical, and Physiological Analysis.

Gram staining was carried out according to standard protocols (9). Scanning electron microscopy (SEM) observations were performed on fixed material prepared for routine examination using the following procedure: A concentrated bacterial suspension was immersion-fixed in a solution of 2.5% glutaraldehyde in 0.1 M cacodylate buffer (pH 7.2). Fixation was allowed to proceed overnight at 4° C. Fixed material was collected by centrifugation and rinsed with cacodylate buffer three times for one hour. Samples were then post-fixed with an osmium tetroxide solution (1.0% OsO4 and 1.5% ferrocyanide in cacodylate buffer) for one hour and dehydrated by successive immersion in a graded ethanol series (25, 50, 75, 95, and 100% v/v EtOH) for 20–30 min each. Dehydrated samples were critical point dried, mounted on stubs, and sputter coated with a gold/palladium mixture. The cells were visualized using a Hitachi S-4000 scanning electron microscope (Tokyo, Japan) equipped with a field emission electron source. Digitized images were collected with an iXRF digital image capturing system (IXRF Systems, Houston, Tex.). Morphology is shown in FIGS. 7A& B and 10–13.

A dehydrated carbon source utilization test was based on a set of 49 organic compounds and was performed using the API50CH system (Biomerieux, Montalieu-Vercieu, France). In addition, the isolated bacterium was cultivated in 50-ml conical flasks on minimal liquid medium supplemented with 1.2 g $L^{-1}$ of $NH_4NO_3$ (3.0 mM N) and various carbon sources added to a final concentration of 0.5% v/v (liquid substrates) or 5 g $L^{-1}$ (solid substrates), except formaldehyde, 0.05% v/v; TNT, 1.0 g $L^{-1}$; RDX, 1.0 g $L^{-1}$; and HMX, 1.0 g $L^{-1}$. Flasks were inoculated and incubated for one week at room temperature with agitation. Carbon source utilization was determined by the biomass dry weight after two weeks of incubation. A biochemical test based on a set of 19 enzymatic assays was performed using API ZYM system (Biomerieux).

The bacterium was shown to grow on different $C_1$-carbon sources, including methanol, methylamine, and formaldehyde, which is a particular attribute of the genus Methylobacterium. Other carbon substrates sustaining growth of Methylobacterium sp. BJ001 included fructose, glycerol, ethanol, and a wide range of organic acids. On the other hand, no growth was observed on saccharose, arabinose, galactose, iso-propanol, n-butanol, chloromethane, dichloromethane, TNT, RDX, or HMX. Using further biochemical assays, strain BJ001 tested positive for the following enzymatic reactions: Akline phosphatase, esterases ($C_4$ and $C_8$), valine arylamidase, α-chymotrypsine, acid phosphatase, and naphtol-AS-BI-phosphohydrolase.

D. Characterization of the Isolated Bacterium by 16S and 16S-23S IGS rDNA Analysis.

General techniques for DNA manipulations were carried out according to standard protocols (1,39). Bacterial genomic DNA was extracted by centrifugation from 4-day pre-grown cell suspensions using a DNeasy Tissue Kit (Qiagen, Inc., Valencia, Calif.). Extracted DNA was further purified by phenol-chloroform extraction and ethanol precipitation (1). For 16S rDNA PCR amplification, the following universal primers were synthesized: Forward bacterial primer 27f (positions 11–27 of bacterial 16S rDNA, according to Escherichia coli numbering) and reverse bacterial primer 1513r (positions 1492–1513 of bacterial 16S rDNA, E. coli numbering). For 16S-23S IGS rDNA amplification, a forward primer 926f (positions 901–926 of bacterial 16S rDNA, E. coli numbering) and a reverse primer 1115r/23S (positions 97–115 of bacterial 23S rDNA, E. coli numbering) were used (49). PCR amplifications were carried out on a Matercycler Gradient (Eppendorf A G, Hamburg, Germany) by the following steps: Initial denaturation at 94° C. for 3 min; 30 cycles of denaturation at 94° C. for 1 min, elongation at 54–56° C. for 1 min, and extension at 72° C. for 90 sec; and final extension at 72° C. for 10 min (49). PCR products were first analyzed by agarose gel electrophoresis (AGE) according to standard protocols (39). PCR products were then purified using a Qiagen PCR Purification Kit. Retrieved sequences were submitted for sequencing at the University of Iowa DNA Core Facility (Iowa City, Iowa). Sequencing was carried out by Sanger-based fluorescent identification of bases on an ABI 3700 electrophoresis detector (The Institute for Bioanalytics, Branford, Conn.) and using separately both the forward and the reverse primers used for amplification. The determined rDNA sequences, as well as reference sequences retrieved from NCBI GenBank (U.S. National Library of Medicine, Bethesda, Md.), were aligned by ClustalW Multiple Alignement, BioEdit (version 5.0.9.) software (Raleigh, N.C.). The tree topology was inferred by the "neighbor-joining" method using Mega2 (version 2.1.) software (27).

16S and 16S-23S IGS rDNA sequences from Methylobacterium sp. BJ001 (ATCC PTA-5125; NCIMB 13946) have been deposited to NCBI GenBank database under the accession numbers AY214142 and AY214143 respectively (both sequences are provided in FIG. 8). The accession numbers for the sequences used in the phylogenic analysis are as follows: Agrobacterium tumefaciens, D14500; Escherichia coli, J01859; Hirschia baltica, M52909; Magnetospriullum magnetotacticum, M58171; Methanococcus vannielii, M36507; M. extorquens, D32224; M. mesophilicum, AJ400919; M. nodulans, AF220763; M. organophilum, D32226; M. radiotolerans, D32227; M. rhodesianum, D32228; *M. rhodinum*, D32229; *M. zatmanii*, L20804; *Methylosinus sporium*, M95665; *Pseudomonas aeruginosa*, X06684; *Rhodobium marinum*, D30790; *Rhodoplanes roseus*, D25313; *Rhodopseudomonas palustris*, D25312; and *Sphingomonas paucimobilis*, D13725.

Figure 2:
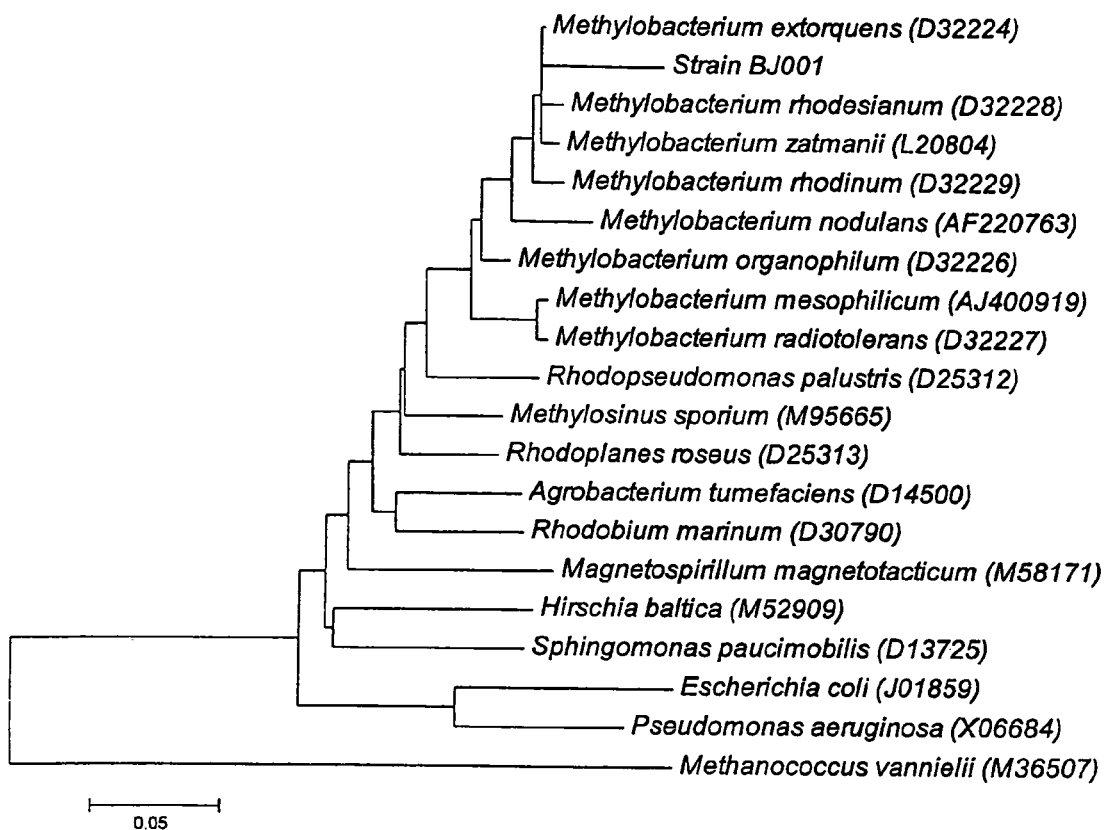
FIG. 2 shows results of a phylogenetic analysis of 16S rDNA sequences from members of the genus *Methylobacterium* and other representatives of α-2 *Proteobacterium*, showing the location of strain BJ001 (GenBank Accession No. AY234142). Also shown are representatives of the following bacterial groups: α-i *Proteobacterium, Magnetospirillium magnetotacticum*; α-3 *Proteobacterium, Hirschis baltica*; α-4 *Proteobacterium, Sphingomonas paucimobilis*; β *Proteobacterium, Escherischia coli*; γ *Proteobacterium, Pseudomonas aeruginosa*; and Archeobacteria, *Methanococcus vannielii*. NCBI Genbank accession numbers are provided in parentheses.

Using 16S ribosomal DNA (rDNA) and 16S-23S intergenic spacer (IGS) rDNA analysis as described above, the isolated strain was identified as a *Methylobacterium* sp. A phylogenetic tree based on the 16S rDNA sequence and showing the location of *Methylobacterium* sp. BJ001 is displayed in FIG. 2 (see also the phylogenetic tree of FIG. 9, described in Example 2, which includes additional *Methylobacterium* species). Phylogenetic relationships were confirmed by 16S-23S IGS rDNA analysis (data not included). According to the sequence similarity matrix, the closest relatives to *Methylobacterium* sp. BJ1001 are *M. thiocyanatum, M. extorquens, M. zatmanii*, and *M. rhodesanium*, with 99.3, 99.1, 98.6, and 98.5% 16S rDNA sequence similarities, respectively. Further detail regarding phylogenetic placement is provided in Example 2, below.

Identified *Methylobacterium* sp. BJ001 isolated from poplar tissues (*Populus deltoides×nigra* DN34) belongs to the α-2 subclass of *Proteobacteria* and, as noted above, has been shown to be related to *M. extorquens*. *M. extorquens* is a widely distributed methylotrophic bacterium, frequently associated with plant leaves and roots (51). Members of the genus *Methylobacterium* are known to be common inhabitants of the rhizosphere and the phyllosphere of plants and have been described as chronic contaminants of plant tissue cultures (20, 21, 30, 51). However, this is the first identified close association between a *Methylobacterium* species and a poplar tree (*Populus* sp.).

A transient red coloration of plant tissues, as well as red colonies spreading only from wounded plant materials, suggests that *Methylobacterium* sp. BJ001 is an endophyte. Surface sterilization of original explants and manipulations under sterile conditions should ensure microbe-free plant tissues, except in the case of endophytic bacteria. A recently identified fourth branch of *rhizobia* (a heterogenous clade gathering bacteria fixing nitrogen in symbiosis with leguminous plants) includes members of the genus *Methylobacterium* (47). The ability shown by *Methylobacterium* sp. BJ001 to grow on nitrogen-free medium suggests that the bacteria can fix atmospheric nitrogen. The ability of *Methylobacterium* sp. BJ001 to metabolize fructose faster than any other carbon sources—fructose is the first hexose produced by photosynthesis—also supports an endophytic ecology.

E. Compositions Comprising *Methylobacterium* Species, Including the Novel Strain BJ001

Compositions comprising the *Methylobacterium* species disclosed herein are provided according to one aspect of the invention. Such compositions include, for example, a composition comprising an isolated *Methylobacterium* having all identifying characteristics of the *Methylobacterium* sp. BJ001 deposited with ATCC at Accession No. PTA-5125, and at NCIMB at Accession No. 13946, or other *Methylobacterium* species, and such a composition further comprising a nitramine or nitroaromatic compound or compounds. The nitramine or nitroaromatic compound or compounds can be, for example, an explosive or a derivative (e.g., a partial breakdown product) thereof. The explosive can be, for example, TNT, RDX or HMX or derivatives thereof described herein below or known in the art.

Uses of *Methylobacterium* Species

The nitramine- and nitroaromatic-compound degrading capacities of the *Methylobacterium* species disclosed herein can be exploited for the decontamination of sites and materials contaminated with such compounds. Exemplary nitramine and nitroaromatic compounds and approaches to their degradation and decontamination of such sites and materials are described herein below.

A. Nitramine and Nitroaromatic Compounds

A number of nitramine and nitroaromatic compounds can be substrates for degradation by the novel *Methylobacterium* species described herein. These include, but are not limited to 2,4,6-trinitrotoluene (TNT) and degradation products or derivatives thereof (e.g., 2,4-dinitrotoluene, 4-amino-2,6-dinitrotoluene), octahydro-1,3,5,7-tetranitro-1,3,5,7-tetrazocine (HMX) and degradation products or derivatives thereof (e.g., octahydro-1,3,5-trinitro-7-nitroso-1,3,5,7-tetrazocine, octahydro-1,3-dinitro-5,7-dinitroso-1,3,5,7-tetrazocine, octahydro-1,5-dinitro-3,7-dinitroso-1,3,5,7-tetrazocine, octahydro-1-nitro-3,5,7-trinitroso-1,3,5,7-tetrazocine, octahydro-1,3,5,7-tetranitroso-1,3,5,7-tetrazocine), 1,3,5-trinitro-1,3,5-triazine (RDX) and degradation products and derivatives thereof (e.g., hexahydro-1-nitroso-3,5-dinitro-1,3,5-triazine (MNX), hexahydro-1,3-dinitroso-5-nitro-1,3,5-triazine (DNX), and hexahydro-1,3,5-trinitroso-1,3,5-triazine (TNX). *Methylobacterium* sp. BJ001 is shown herein to degrade TNT, HMX and RDX. Because TNT (a representative nitroaromatic compound), and RDX and HMX (representative nitramines) present chemical structures and moieties that are characteristic of their respective groups of compounds, the metabolic chemistry applied by the *Methylobacterium* species described herein to degrading any of various nitroaromatics and nitramines would be substantially the same as applied to TNT, HMX and RDX. For example, degrading a nitroaromatic would require removal of the nitro groups and cleavage of the aromatic ring(s). The fact that the isolated strain can rapidly degrade TNT indicates that the strain would be capable of degrading any of various other nitroaromatics. Similarly, degrading a nitramine would require removal of nitro groups and cleavage of the alkylamino backbone of the molecule. The fact that the isolated strain can efficiently degrade RDX and HMX indicates that the strains would be capable of degrading any of various other nitramines. Other nitroaromatic compounds may include, for example, nitrobenzene, all isomers of dinitrobenzene (e.g., 1,3-dinitrobenzene), trinitrobenzene (e.g., 1,3,5-trinitrobenzene), nitrotoluene (e.g., 2-nitrotoluene), dinitrotoluene (e.g., 2,4-dinitrotoluene), trinitrotoluene (e.g., 2,4,5-trinitrotoluene), nitrophenol (e.g., 2-nitrophenol), dinitrophenol (e.g., 1,3-dinitrophenol), trinitrophenol (e.g., picric acid), and degradation products or derivatives thereof (e.g., aminobenzene, 1-amino-3-nitrobenzene, 1-amino-3,5-dinitrobenzene, 2-aminotoluene, 2-amino-4-nitrotoluene, 2-amino-4,5-dinitrotoluene, aminophenol, 2-amino-4-nitrophenol, 2-amino-4,6-dinitrophenol). Other energetic compounds may include nitrocellulose, nitroglycerine, pentaerytriol tetranitrate, tetryl, etc. The fact that the isolated strain can efficiently degrade TNT, RDX, and HMX individually indicates that the strain would be capable of degrading mixtures of them, and mixtures of any of the energetic compounds and their degradation products and derivatives thereof listed above. Mixtures of energetic compounds and degradation products and derivatives may originate from blending in the environment as a result of utilization and release of different parent compounds, and/or from the partial in situ biodegradation of parents compounds. Mixture of energetic compounds and degradation products and derivatives may originate from blending before utilization and release in the environment (e.g.,) and/or from the partial in situ biodegradation of original mixtures.

B. Degradation of Nitroaromatic and Nitramine Compounds

In one embodiment, a method is provided for the degradation of nitroaromatic and nitramine compounds in the environment or elsewhere. In general, this involves contacting the compounds with one or more *Methylobacterium* species, including strain BJ001. The *Methylobacterium* sp. BJ001 has an advantage in being a naturally-occurring species found as an endosymbiont of Poplar tissues. The natural occurrence of the bacterium indicates that it is safe to use in the open environment.

In one aspect, contaminated soil, sediment, sludge, or wastewater is contacted with the *Methylobacterium* species. The contaminated material can be contacted with a preparation of the bacteria while the material is still in the environment. For example, the *Methylobacterium* preparation can be applied to open fields, lagoons, ponds, or other areas contaminated with nitroaromatic or nitramine compounds. Methods of application can include, for example, spraying, broadcasting, sowing or otherwise distributing a preparation of the bacteria onto or into the area to be treated. If necessary or desired, the preparation can be mixed into the soil, sediment, sludge or wastewater, for example, by tilling, plowing or stirring. Such mixing can be performed once, upon application, or repeatedly (e.g., 2, 3, 4 or more times) over the course of decontamination, or even continuously during the process. Whereas the *Methylobacterium* species are strictly aerobic, breakdown of contaminants can be aided by increasing the aeration of the material being decontaminated. Thus, in one embodiment, continuous or frequent mixing or turning of the material during the process is preferred. Soil, sediment or water samples from the area being treated can be monitored (e.g., by HPLC as described herein, or by other suitable means, e.g., gas chromatography/mass spectrometry (GC/MS)) for nitroaromatic and nitramine contaminant levels at various time intervals (daily, weekly, etc.) to determine the progress of the decontamination.

Where relatively dry soil is to be decontaminated in the open environment, it can be beneficial to increase the hydration of the soil in order to encourage growth of the bacteria. This can be accomplished through standard irrigation means well known to those skilled in the art. Care should be taken in the process, however, to avoid increasing runoff or spreading of contaminants in the irrigation water. Generally, water should not exceed about 50% of the moisture-holding capacity of the soil.

In another aspect, contaminated soil, sediment, sludge, wastewater or other contaminated material is removed from the open environment and contacted with the *Methylobacterium* species in isolation, for example, in a container or trough. Preferably such container is lined. This approach is referred to herein as "composting," and can be particularly useful, as a non-limiting example, in situations in which the level of contamination is particularly high, such that the contaminant(s) present a toxic threat to the bacteria themselves. In this situation, it can be helpful to compost the material by first mixing it with an amount of non-contaminated material, e.g., soil, manure, wood chips, potato scraps, apple pomace, or other material that effectively dilutes the concentration of contaminant(s) to a level wherein the bacteria are not killed, thereby permitting them to degrade the contaminant(s). These or other additional materials can also be added to provide nutrients to maintain the health of the bacteria. The composting can be performed under controlled conditions of pH (ranging from about pH 3.0 to about pH 11.0, preferably about pH 6.0 to about pH 8.0), temperature (about 4° C. to about 41° C., preferably about 15° C. to about 37° C.), oxygen (about 5% to about 100% saturation, preferably about 20% to about 100% saturation) and hydration (to about 40% wt/wt). After inoculation, the contents of the container can be turned or agitated so as to maintain aeration and ensure contact of the bacteria with contaminants to be degraded. Samples of the composting material can be monitored by, for example, HPLC or other suitable method, to follow the progress of decontamination. It is contemplated that the process could be scaled up from a "batch" process to a continuous feed process, wherein the material is slowly moved through zones in the container as new material is added behind it, emerging from the end after full decontamination. Composting as a general means of degrading nitroaromatic and nitramine compounds such as TNT, RDX and HMX is also described by, for example, Williams et al., 1992, J. Ind. Microbiol. 9: 137–144, Griest et al., 1993, Environ. Toxicol. Chem. 12: 1105–1116, Jarvis et al., 1998, Ecotoxicol. Environ. Safety 39: 131–135 and Bruns-Nagel et al., 2000, Composting (Humification) of Nitroaromatic Compounds. In: Spain et al., (eds) Biodegradation of Nitroaromatic Compounds and Explosives. CRC Press, Boca Raton, pp 357–394.

In yet another aspect, the material to be decontaminated can be mixed with water to create a slurry of the material, for example, about a 30% w/w slurry. Bacteria are added and the slurry is fermented or cultured under conditions conducive to the decontamination of the slurry by the bacteria. Conditions such as pH (ranging from about pH 3.0 to about pH 11.0, preferably about pH 6.0 to about pH 8.0), temperature (about 4° C. to about 41° C., preferably about 15° C. to about 37° C.), and oxygen (about 5% to about 100% saturation, preferably about 20% to about 100% saturation) can be controlled in the slurry. The slurry should be agitated or stirred to maximize both contact of contaminants with the bacteria and aeration. As above, additional nutrients can be added if necessary or desired. Samples can be monitored at various intervals by, for example, HPLC in order to follow the decontamination process.

Where necessary or desired, removal of contaminated material from an environmental site to a site for bioremediation as described herein can be accomplished, for example, by excavation and transport using equipment well known in the field. Where the contaminated material is, for example, wastewater or runoff, the liquids can be pumped from the site and transported by standard methods of transporting liquids. Alternatively, contaminated liquid materials can be absorbed with, for example, paper or other absorbent materials, and those materials now containing the contaminated water can be transported to a facility for decontamination.

In each of the aspects described herein, it is contemplated that other bacteria (including other members of the genus *Methylobacterium*) can also be added for their combined effect on the decontamination process. Additional microbes can be naturally present in, for example, livestock manure. Where manure is used in any aspect of the methods or compositions described herein, it is preferable to avoid manure from animals, e.g., cattle, that are routinely treated with antibiotics, as the antibiotics may have adverse effects on the *Methylobacterium*. One source that does not tend to be tainted with antibiotics is horse manure.

Other microbes that can be included in preparations of the *Methylobacterium* species include, as non-limiting examples, aerobic microbes such as *Pseudomonas* species (e.g., *P. fluorescens* (e.g., ATCC 12842), *P. aeruginosa* (e.g., ATCC 10145), *P. pseudoalcaligenes* JS52 (Fiorella & Spain, 1997, Appl. Environ. Microbiol. 63: 2007–2015), *P. savastanoi* (e.g., ATCC 13492), *P. putida* (e.g., ATCC 17391), *Pseudomonas* strain CIS1 (Duque et al., 1993, J. Bacteriol. 175: 2278–2283), *Rhodococcus* species (e.g., *R. erythropolis* HLPM-1; Lenke & Knackmuss, 1992, Appl. Environ. Microbiol. 58: 2933–2937), *Enterobacter* sp (e.g., *E. cloacae*, French et al., 1998, Appl. Environ. Microbiol. 64: 2864–2868), and *Mycobacterium* sp. (E.g., *Mycobacterium vaccae* (Vanderberg et al., 1995, Appl. Microbiol Biotechnol. 43: 937–945), among others. Preparations of anaerobic bacteria can also be combined with preparations of the *Methylobacterium* species described herein, including, as non-limiting examples, *Clostridium* species (e.g., *C. bifermentans* (e.g., ATCC 17836), *C. acetobutylicum* (e.g., ATCC 39236) and others. Sulfate-reducing bacteria can also be included in compositions with the *Methylobacterium* species described herein, including, as a non-limiting example, *Desulfovibrio* species. Fungi, including for example, white rot fungi species such as *Phanerochaete chrysosporium* (e.g., ATCC 34541) and *Phlebia radiata* (e.g., ATCC 52891), can also be included. Further microbial isolates that can be included with the *Methylobacterium* species described herein include, for example, those *Arthrobacter* species described in U.S. Pat. No. 5,478,743, incorporated herein by reference (ATCC Accession Nos. include, for example, 55546, 55547, 55548 and 55549), microbial species described in U.S. Pat. No. 5,455,173, incorporated herein by reference (e.g., ATCC Accession Nos. 55559, 55560, and 55561), and members of the consortium of species disclosed in U.S. Pat. No. 5,543,324 (e.g., the consortia at ATCC Accession No. 55381 and 55382, which include, for example, *Arthrobacter uratoxydans, Aurobacterium saperdae, Bacillus cereus, Flavobacterium esteroaromaticum, Micrococcus luteus, Micrococcus varians, Pseudomonas putida* and *Ochrobacterium anthropi*), among others.

Where microbes in addition to the *Methylobacterium* species described herein are employed, the proportion of *Methylobacterium* species to other microbe(s) can range from, for example, about 1000:1 to about 1:1000, e.g., about 500:1, about 200:1, about 100:1, about 10:1, about 1:1, about 1:10, about 1:100, or about 1:200. These proportions can be an organism to organism ratio or, for example, a weight to weight ratio.

The *Methylobacterium* species preparation can be provided in the form of a liquid suspension or slurry that is sprayed onto or into a material to be decontaminated. Dried preparations of the bacteria can also be used for inoculation, and are discussed herein above.

C. Determination of Nitroaromatic and Nitramine Compound Degradation

For degradation in experimental cultures, the analysis of nitro-substituted compounds (e.g., TNT, RDX, HMX, and their metabolites) can be performed by reverse phase HPLC (HP Series 1100; Hewlett-Packard, Palo Alto, Calif.) on a $C_{18}$ Supelcosil® LC-18 column (25 cm×4.6 mm, 5 µm; Supelco, Bellefonte, Pa.). The system is equipped with a UV-visible photodiode array detector (HP Series 1100), a mass spectrometry detector (Agilent 1100 Series LC/MSD, Palo Alto, Calif.), and a Radiomatic Flo-One β radiochromatograph (Packard Bioscience, Meriden, Calif.) for the detection of $^{14}C$-radioactive compounds. The mobile phase consists of AcCN:0.1% w/v ammonium acetate ($NH_4CH_3COO$) running at a flow rate of 1 ml $min^{-1}$. For mass analyses, a Zorbax 80 Å Extended-$C_{18}$ column (2.1× 100 mm, 3.5 µm; Agilent) running at flow rate of 0.2 ml $min^{-1}$ is used. The mass spectrometer is equipped with an electrospray ionization source (ESI) used in negative mode. Operating parameters are as follows: Capillary voltage, 3.0 kV; drying gas flow, 12.01 $min^{-1}$; nebulizer pressure, 35 psig; drying gas temperature, 350° C. TNT and its metabolites are detected by their M-H ion masses, while RDX, HMX, and their metabolites were detected by their M+60-H (acetate) ion masses. $^{14}C$-Radioactivity in solution, in extracts, and in $CO_2$ traps is analyzed with a Beckman liquid scintillation counter (LSC) LS 6000IC (Beckman Coulter, Fullerton, Calif.) using Ultima Gold XR® (Packard Bioscience) as scintillation cocktail.

Radioactivity remaining in cells is analyzed by biooxidation using a biological oxidizer Harvey OX600 (R. J. Harvey Instrument, Hillsdale, N.J.). $^{14}CO_2$ contained in outgoing gases was trapped into 10 ml of $^{14}Carbon$® scintillation cocktail (R. J. Harvey Instrument) and the radioactivity is determined by LSC.

Bacterial growth is recorded by the OD at 600 nm and the biomass dry weight. Cell dry weight is determined by harvesting cells by filtration on glass fiber and drying overnight at 105° C. Cell concentration is determined by direct counting using a hemocytometer (Hausser Scientific, Horsham, Pa.). Photometric data are converted to biomass dry weight and to cell concentration using standard curves.

For the determination of degradation of nitroaromatic and nitramine compounds, such as TNT, RDX and HMX in, for example, environmental samples being decontaminated as described herein, HPLC can be used as for experimental analyses described above, as can other suitable methods of analysis. With an HPLC instrument, detection of the subject compound and its transformation and degradation products can be performed using a diode-array detector, measuring UV absorption at selected absorption maxima and/or continuouos scanning over a suitable wavelength range. The U.S. Environmental Protection Agency (EPA) has a standard set of conditions used to measure nitroaromatics and nitramines in soil. This method, referred to as Method 8330, titled "Determination of Concentration of Nitroaromatics and Nitramines by High-Performance Liquid Chromatography (HPLC)" is incorporated herein by reference and summarized below:

EPA Method 8330 provides three optional procedures for low concentration (parts per billion (ppb) or nanograms per liter (ng $L^{-1}$) of certain explosives residues in surface or ground water. These options are salting-out extraction, cartridge solid-phase extraction, and membrane solid-phase extraction. Direct injection of diluted and filtered water samples can be used for water samples of higher concentration, and a similar method is used for soils and sediments.

EPA Method 8330 Low-Level Method No. 1: Salting-Out with No Evaporation:

Aqueous samples of low concentration are extracted using a salting-out extraction procedure with acetonitrile and sodium chloride. The small volume of acetonitrile that remains undissolved above the salt water is drawn off and transferred to a smaller volumetric flask. It is back-extracted by vigorous stirring with a specific volume of salt water. After equilibration, the phases are allowed to separate, and the small volume of acetonitrile residing in the narrow neck of the volumetric flask is removed using a Pasteur pipette. The concentrated extract is diluted 1/1 with reagent-grade water. An aliquot is separated on a C-18 reverse-phase column, determined at 254 nm, and confirmed on a CN reverse-phase column.

EPA Method 8330 Low-Level Method No. 2: Cartridge Solid-phase Extraction:

Extraction cartridges are fitted with frits at one end, then packed tightly with Porapak RDX. A second frit is placed over the open ends of the cartridges to retain the material inside. Using a Visiprep Solid-Phase Extraction Manifold (Supelco), the aqueous samples are extracted through the cartridges; the cartridges are then eluted using acetonitrile. The resulting eluate is diluted 1/1 with reagent-grade water prior to analysis.

EPA Method 8330 Low-Level Method No. 3: Membrane Solid-Phase Extraction:

Empore styrene-divinyl benzene (SDB) RPS disks are placed in a vacuum filter apparatus and soaked with acetonitrile. The acetonitrile is pulled through the disk, followed by reagent-grade water. Just before all the water has been pulled through, the vacuum is turned off and an aqueous water sample aliquot is placed in the reservoir. Turning the vacuum back on, the aliquot and any remaining water is pulled through the membrane. Air is then pulled through the disks for a short time to remove any excess water. Once they are dry, acetonitrile is added to the reservoir and allowed to soak into the membrane. Next, the acetonitrile is pulled through the disks into a test tube that has been fitted into the vacuum flask. The resulting extract is removed using a Pasteur pipette and placed into a graduated cylinder where it is diluted 1/1 with reagent-grade water prior to analysis.

EPA Method 8330 High-level Direct Injection Method:

Aqueous samples of higher concentration can be diluted 1/1 (v/v) with methanol or acetonitrile, filtered, separated on a C-18 reverse-phase column, determined at 254 nm, and confirmed on a CN reverse-phase column. If HMX is an important target analyte, methanol is preferred.

EPA Method 8330 Method for Soil and Sediment Samples:

Soil and sediment samples are extracted using acetonitrile in an ultrasonic bath, filtered, and chromatographed, as in the high level direct injection method.

Another method for determining the amount of degradation of a nitrogen-containing compound such as a nitroaromatic or nitramine compound is to analyze the amount of nitrite released during the degradation process. Methods for determining the amount of nitrite released from nitrogen-containing compounds are common and well known in the art. For example, Misko et al. (Anal. Biochem., 214, 11, (1993)) teach a fluorometric assay for the measurement of nitrite in biological samples which is designed to detect nitrite/nitrate. The method is based upon the reaction of nitrite with 2,3-diaminonaphthalene to form the fluorescent product, 1-(H)-naphthotriazole. Carson et al. (U.S. Government Report, DC/WRRC-42, W83-02296, OWRT-A-019-DC(1); Order No. PB83–180331, 31 pp. From: Gov. Rep. Announce. Index (U.S.) 1983, 83 (14), 3113) discuss the determination of nitrite and nitrate in water by reduction to ammonia followed by enzymatic cycling involving the reduction of $NO_2^-$ and/or $NO_3^-$ to $NH_3$ with Devarda's metal while simultaneously trapping the released $NH_3$ gas with diluted aqueous HCl. Another nitrite release assay is the method described by Smibert et al. (Method I in Manual of Methods for General Bacteriology, Gerhardt, Murray, Costilow, Nester, Wood, Kreig & Phillips, Editors, p. 419 (1981)). This method involves the colorometric detection of nitrite by mixing a sample suspected of containing nitrite with N-1-naphthyl ethylenediamine HCL and sulfanilic acid, with detection at 540 nm.

Measurement of the levels of total organic carbon (TOC) in culture media is another indication of the level of degradation of microbial carbon sources. Methods for the determination of TOC are common and well known in the art and any suitable method can be used. Sakamoto et al. (Ultrapure Water, 4(9), 24, 26–8, 30–1 (1987)) discuss a method for measuring TOC by wet oxidation and Heanes (Commun. Soil Sci. Plant Anal., 15(10), 1191–213 (1984)) teaches the determination of total organic carbon in soils using chromic acid digestion followed by a spectrophotometric procedure. A review of several methods is provided by Haverty (Ultrapure Water, 1(2), 29–31 (1984)).

Nitroaromatic and nitramine compounds are considered "degraded" when one or more chemical bonds in a nitroaromatic or nitramine target compound are broken. Degradation preferably continues to completion, that is until mineralization of the compound to $H_2O$ and $CO_2$ and where none of the starting material is present. However, degradation to a form having reduced toxicity relative to the starting compound(s) is beneficial.

EXAMPLES

Example 1

Degradation of Nitroaromatic and Nitramine Explosives

Cell suspensions of *Methylobacterium* sp. strain BJ001 in pure culture were exposed separately to nitro-substituted explosives TNT, RDX, and HMX. Bioreactors consisted of 250-ml conical flasks equipped with lateral tubing for sample collection and closed by a rubber stopper. Flasks were equipped with a $CO_2$ trap consisting of a 5-ml glass vial containing 1 ml of 1.0 N NaOH. Each bioreactor contained 100 ml of liquid LB medium supplemented with $^{14}C$[-U-ring]-TNT (25 mg $L^{-1}$), $^{14}C$[-U-ring]-RDX (20 mg $L^{-1}$), or $^{14}C$[-U-ring]-HMX (2.5 mg $L^{-1}$). Each flask was inoculated with a concentrated cell suspension (1.0% v/v). The inoculum was prepared from a 48-h old log-phase cell suspension growing in LB medium supplemented with methanol (0.5% v/v) or fructose (0.5% w/v) and incubated under stirring at 28° C. Cells were harvested by centrifugation (30 min, 5,000 rpm) and re-suspended in sterile DI water. The procedure was repeated two times in order to wash the bacterial cells and the final inoculum exhibited an $OD_{600}$ of 1.0 (i.e. approximately $10^9$ cells $ml^{-1}$). Bioreactors were incubated at room temperature under agitation (125 rpm). One-ml samples of the solution and the $CO_2$ traps were collected periodically for analysis. Control experiments were carried out with non-inoculated flasks or flasks inoculated with the bacteria, but without toxic compound. Experiments were conducted in triplicate.

Figure 3:
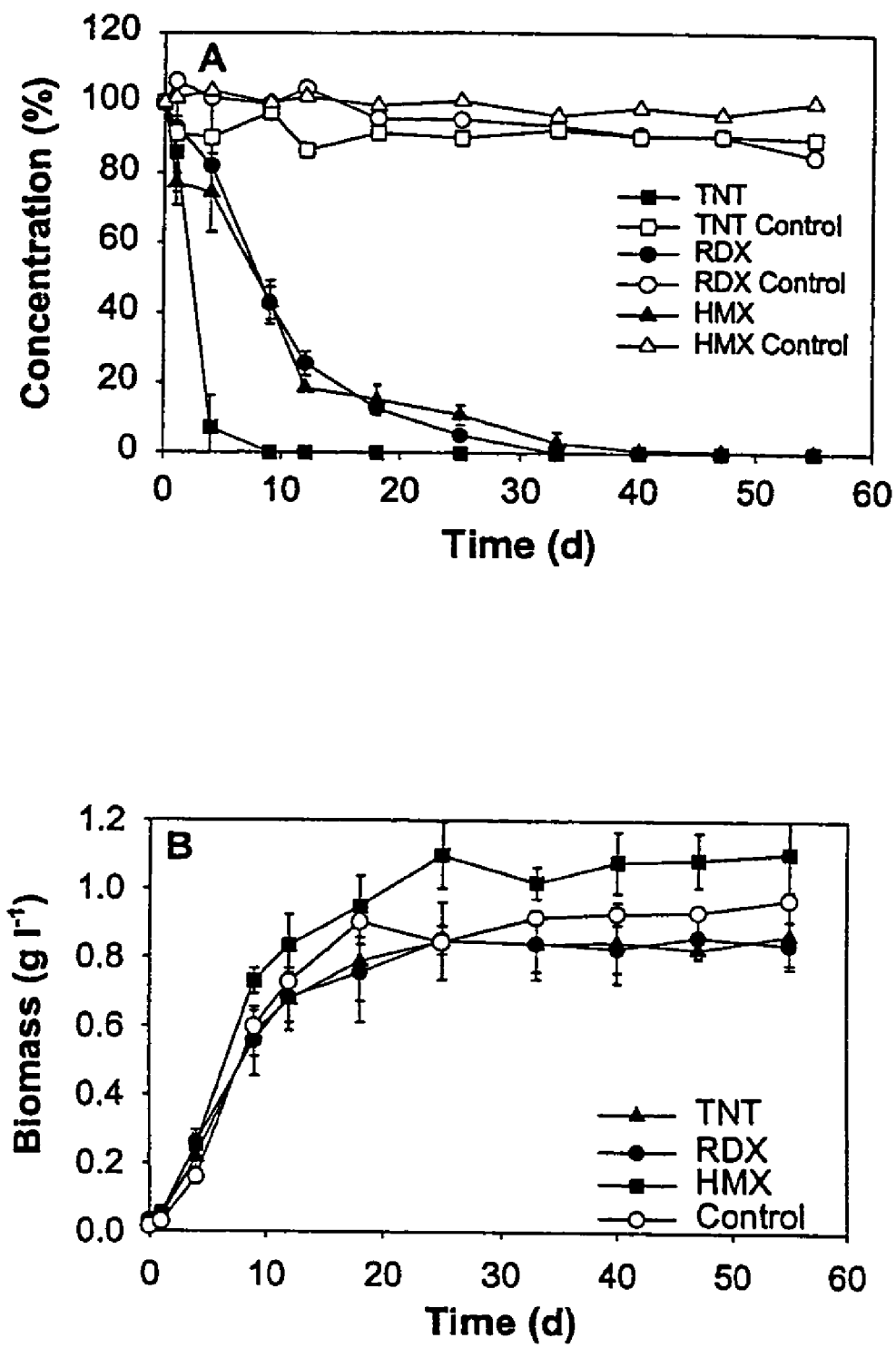
FIGS. 3A and B shows graphical representations of data for the transformation of $^{14}C$-TNT (25 mg $L^{-1}$), $^{14}C$-RDX (20 mg $L^{-1}$), and $^{14}C$-HMX (2.5 mg $L^{-1}$) by pure cultures of *Methylobacterium* sp. BJ001. (A) TNT, RDX, and HMX concentrations remaining in solution are shown. Quantifications are based on the UV absorbance. Control experiments consisted of non-inoculated bioreactors. Concentrations are expressed in percentage of the initial level. (B) Biomass growths in the presence of TNT, RDX, and HMX are presented. Control experiment was conducted without nitrosubstituted explosives.

Bacteria were shown to fully transform the nitro-substituted explosives over the 55 days of experiment (FIG. 3A). Bacterial biomasses (monitored by the $OD_{600}$) showed typical growth curves with an exponential phase (until approximately day 12) followed by a stationary phase (FIG. 3B). By comparison to the control bioreactor, bacterial growth was not significantly affected by the presence of TNT, RDX, or HMX.

While TNT disappeared completely in less than 10 days, no significant mineralization (i.e. release of $^{14}CO_2$) or decrease of the radioactivity in solution was observed (Table 1). In contrast, RDX and HMX concentrations decreased more slowly (reaching non-detectable levels after 40 days), but with a significant release of $^{14}CO_2$, corresponding to 58.0±3.0 and 62.0±3.9% of the initial radioactivity respectively (FIG. 4 and Table 1). As a consequence, the radioactivity remaining in solution decreased to 12.8±1.5 and 12.5±1.3% of the initial dose after 55 days. Radio-chromatograms of the $CO_2$ traps showed only a single peak, identified as aqueous $^{14}CO_2$ by comparison with a $NaH_{14}CO_3$ standard. No significant mineralization or change in the initial concentration or radioactivity was observed in control experiments.

Radiochromatograms of the solution initially containing $^{14}$C-TNT showed a single peak eluted after 18.9 min, which corresponded to TNT (FIG. 5A). After 4 days of treatment, the radioactivity was distributed into 3 peaks eluted after 15.0, 5.1, and 2.7 min respectively. At the end of the experiments, the radioactivity was concentrated in a single peak eluted after 2.7 min. Spectral analysis of the second and third peaks (eluted after 15.0 and 5.1 min) gave masses of 196 (M–H) and 166 (M–H) respectively, suggesting the presence of aminodinitrotoluenes (ADNTs) (MM=197) and diaminonitrotoluenes (DNATs) (MM=167). The profile of metabolite formation showed the transient appearance of ADNTs and DNATs, reaching a maximum after 4 and 18 days respectively, and the final accumulation of unknown compound(s), accounting for 94.3% of the initial radioactivity.

Figure 5B:
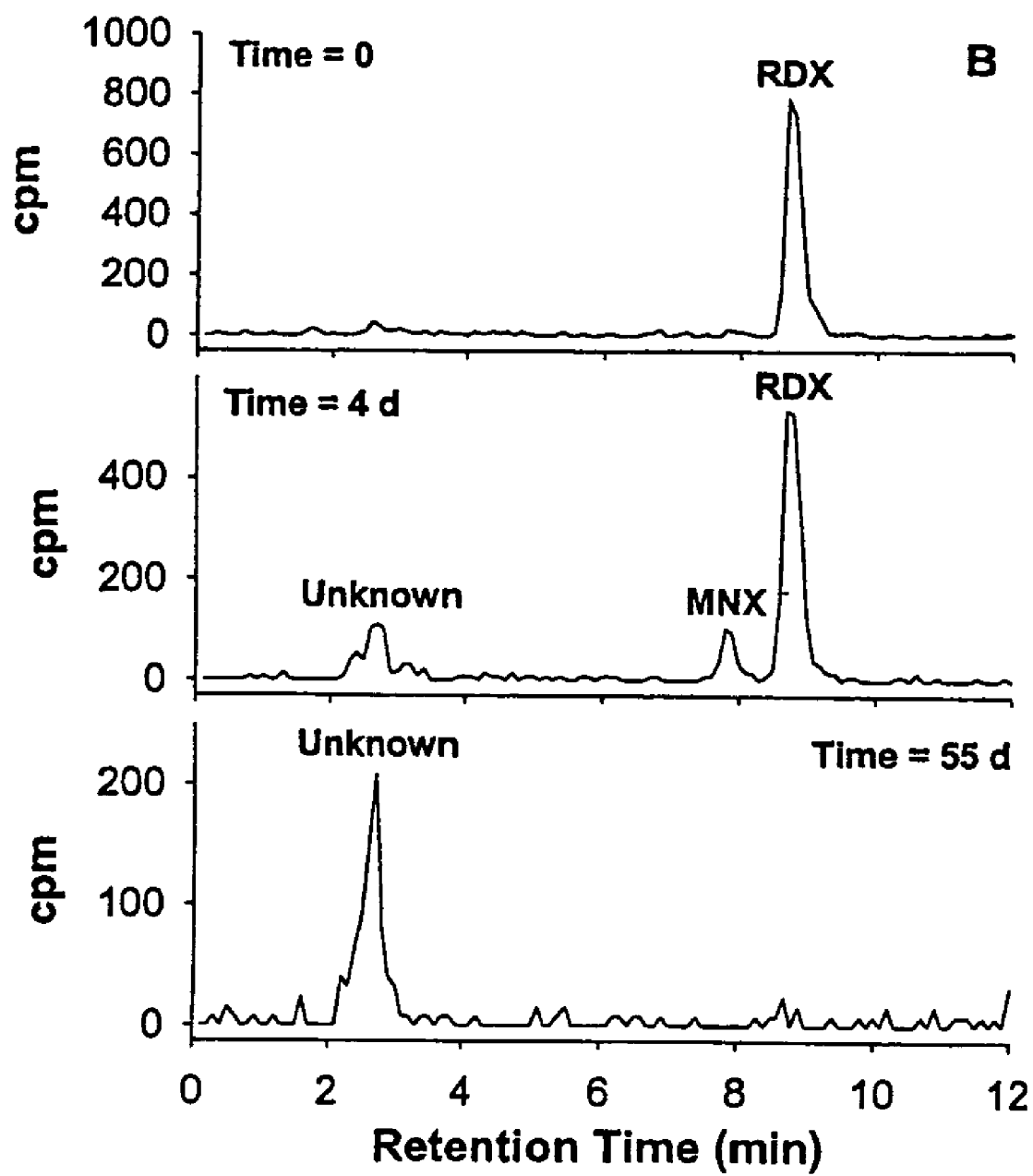

Radiochromatograms of the solution containing RDX at the beginning of the experiment showed a single peak eluted after 8.7 min (FIG. 5B). After 4 days, the remaining radioactivity was concentrated in three peaks eluted after 8.7, 7.8, and 2.7 min respectively. Remaining radioactivity after 55 days was concentrated in a single peak eluted after 2.7 min. The first peak (eluted after 8.7 min) was characterized by a mass of 281 (M+60-H) and corresponded to initial RDX. The second peak (7.8 min) was characterized by mass of 265 (M+60-H) and was identified as the mono-nitroso derivative of RDX (MNX). The final metabolite(s) eluted after 2.7 min exhibited an ion mass of 135 (M–H) suggesting the generation of methylenedinitramine ($O_2NNHCH_2NHNO_2$). The concentration of MNX reached a maximum after 4 days before decreasing slowly to an undetectable level. Unidentified metabolite(s) accumulated in the solution and accounted for 14.9% of the initial radioactivity after 55 days. In addition to mass analysis, DANTs, DANTs, and MNX were identified by comparison of their retention times and UV spectra with authentic standards.

Analyses of nitro-substituted compounds (i.e. TNT, RDX, HMX, and their metabolites) were performed by reverse phase HPLC (HP Series 1100; Hewlett-Packard, Palo Alto, Calif.) on a $C_{18}$ Supelcosil® LC-18 column (25 cm×4.6 mm, 5 µm; Supelco, Bellefonte, Pa.). The system was equipped with a UV-visible photodiode array detector (HP Series 1100), a mass spectrometry detector (Agilent 1100 Series LC/MSD, Palo Alto, Calif.), and a Radiomatic Flo-One P radio-chromatograph (Packard Bioscience, Meriden, Calif.) for the detection of $1^4$C-radioactive compounds. The mobile phase consisted of AcCN:0.1% w/v ammonium acetate ($NH_4CH_3COO$) running at a flow rate of 1 ml min$^{-1}$. For mass analyses, a Zorbax 80 Å Extended-$C_{18}$ column (2.1× 100 mm, 3.5 µm; Agilent) running at flow rate of 0.2 ml min$^{-1}$ was used. The mass spectrometer was equipped with an electrospray ionization source (ESI) used in negative mode. Operating parameters were as follows: Capillary voltage, 3.0 kV; drying gas flow, 12.01 min$^{-1}$; nebulizer pressure, 35 psig; drying gas temperature, 350° C. TNT and its metabolites were detected by their M–H ion masses, while RDX, HMX, and their metabolites were detected by their M+60–H (acetate) ion masses.

$^{14}$C-Radioactivity in solution, in extracts, and in $CO_2$ traps was analyzed with a Beckman liquid scintillation counter (LSC) LS 6000IC (Beckman Coulter, Fullerton, Calif.) using Ultima Gold XR® (Packard Bioscience) as scintillation cocktail.

Radioactivity remaining in cells was analyzed by biooxidation using a biological oxidizer Harvey OX600 (R. J. Harvey Instrument, Hillsdale, N.J.). $^{14}CO_2$ contained into outgoing gases was trapped into 10 ml of $^{14}$Carbon® scintillation cocktail (R. J. Harvey Instrument) and the radioactivity was determined by LSC.

Bacterial growth was recorded by the OD at 600 nm and the biomass dry weight. Cell dry weight was determined by harvesting cells by filtration on glass fiber and drying overnight at 105° C. Cell concentration was determined by direct counting using a hemocytometer (Hausser Scientific, Horsham, Pa.). Photometric data were converted to biomass dry weight and to cell concentration using standard curves.

To determine whether the transformation/mineralization of nitro-substituted explosives was metabolic or co-metabolic (i.e., associated or not with a carbon or nitrogen utilization), additional degradation experiments using growing cells were carried out in minimal liquid medium supplemented with the following carbon and/or nitrogen sources (See Table 2): Fructose (5 g L$^{-1}$) and $NH_4NO_3$ (1.2 g L$^{-1}$ or 3 mM N), fructose only, $NH_4NO_3$ only, and no fructose and no $NH_4NO_3$. Bioreactors consisted of 30-ml serum vials equipped with a $CO_2$ trap composed of a 4-ml glass tube containing 500 µl of 1.0 N NaOH. Each bioreactor contained 10 ml of liquid medium supplemented separately with $^{14}$C-[U-ring]-TNT (25 mg L$^{-1}$), $^{14}$C-[U-ring]-RDX (20 mg L$^{-1}$), or $^{14}$C-[U-ring]-HMX (2.5 mg L$^{-1}$) and were inoculated with a concentrated cell suspension (1.0% v/v). Control experiments consisted in the same set of media but without addition of TNT, RDX, or HMX. For each set of experiments, LB medium and non-inoculated minimal medium were used as positive and negative control media respectively. Bioreactors were incubated as previously described.

Similar degradation experiments were carried out with other members of the genus *Methylobacterium*, *M. extorquens* (ATCC 14718), *M. organophilum* (ATCC 27886), *M. rhodesianum* (ATCC 21611) growing on LB medium supplemented with succinate (2.0 g L$^{-1}$).

In all sets of experiments (with and without $^{14}$C-TNT, $^{14}$C-RDX, or $^{14}$C-HMX; see Table 2), only minimal media supplemented with fructose (5.0 g L$^{-1}$) supported bacterial growth (reaching 0.7–1.1 g dry biomass L$^{-1}$ after the 20 days), regardless the presence of a nitrogen source. Significant mineralization of nitramines (accounting for 7.0–7.7% of the initial $^{14}$C-RDX and 5.0–6.8% of the initial $^{14}$C-HMX) were observed under the same conditions, i.e. in the presence of fructose. No significant mineralization of $^{14}$C-TNT was recorded. Mineralization rates of nitramines $^{14}$C-RDX and $^{14}$C-HMX were shown to be higher when the bacteria were grown on LB medium (i.e. 18.1 and 15.5% of the initial radioactivity respectively). Interestingly, nitrogen-free control medium (i.e. without TNT, RDX, or HMX) was able to sustain bacterial growth (reaching 1.1 g dry biomass L$^{-1}$), as long as a carbon source (i.e. fructose) was provided. For all sets of experiments, neither significant biomass growth nor release of $^{14}CO_2$ was recorded in the absence of a carbon source or from non-inoculated control flasks.

The ability to mineralize nitramines RDX and HMX was investigated among other representative members of the genus *Methylobacterium*. *Methylobacterium* strains tested were able to significantly degrade nitramine explosives. Strain BJ001 exhibited higher mineralization rates (Table 3).

The data show that *Methylobacterium* species strain BJ001 transforms TNT and mineralizes RDX and HMX into $CO_2$. The transient generation of reduction derivatives early in the degradation process (i.e. ADNTs and DANTs from TNT, MNX from RDX) indicates that the metabolism of explosives by *Methylobacterium* sp. BJ001 began with a reduction reaction. Bacterial transformation of heterocyclic nitramines frequently involves an initial reduction step (31) and nitroso metabolites have been previously detected, both under aerobic and anaerobic conditions (15, 18). Initial nitroreductase-catalyzed reduction of the nitro groups is known to occur either via a two-electron transfer (type I), generating nitroso derivatives, or via a one-electron transfer (type II), producing nitramine anion radicals (17, 18). The detection of MNX (and possibly methylenedinitramine) indicates that the metabolism of RDX by *Methylobacterium* sp. BJ001 followed a two-electron reduction pathway.

On the other hand, being a highly oxidized molecule, TNT can be reduced by many different organisms (57). The stepwise reduction of the nitro groups, with the subsequent generation of reduction derivatives (i.e. hydroxylaminodinitrotoluenes (OHADNTs), ADNTs, and DANTs), is known to be the major transformation pathway of TNT, even though NADPH-dependent reductive hydrogenation of the aromatic ring (with the formation of (di)hydride-Meisenheimer complex) has been reported (29).

However, following these early reduction steps, the fates of the nitro aromatic explosive TNT and of heterocyclic nitramines RDX and HMX diverge considerably. Indeed, while the metabolism of $^{14}C$-RDX and $^{14}C$-HMX by *Methylobacterium* sp. BJ001 resulted in an extensive release of $^{14}CO_2$, no significant mineralization of $^{14}C$-TNT was observed. Mineralization of RDX and HMX by aerobic bacteria is well documented (17, 53). However, several bacterial strains were reported to convert RDX and HMX into nitroso derivatives, which accumulate in the medium, suggesting that they are neither mineralized nor serving as carbon or nitrogen sources (24). It is a common feature that a slight change in the chemical structure of hetero cyclic nitramines—such as the reduction of a nitro group—destabilizes the entire molecule (inner C—N bonds are less than 2 kcal $mol^{-1}$), resulting in a ring cleavage generating various aliphatic hydroxylamines and nitramines (17, 18, 53). The latter may decompose and/or rearrange, eventually producing methanol ($CH_3OH$), formaldehyde (CHO), $CO_2$, and $N_2O$ (17, 31). However, besides the formation of $^{14}CO_2$, no clear conclusion can be stated about the ability of *Methylobacterium* sp. BJ001 to use heterocyclic nitramines as carbon and/or nitrogen sources. The inability of the bacterium to grow on RDX or HMX when added in high concentration (as applied for carbon source-utilization tests) might be the result of a toxic effect, while concentrations of RDX and HMX as low as 20 and 2.5 mg $L^{-1}$ (as applied for degradation experiments) would hardly sustain a significant bacterial growth on minimal medium. On the other hand, the apparent capacity of *Methylobacterium* sp. BJ001 to fix atmospheric nitrogen prevents any conclusion about the potential use of RDX and HMX as sole nitrogen sources. It is emphasized, however, that whether or not *Methylobacterium* sp. BJ001 can utilize RDX or HMX as a sole carbon and/or nitrogen source has no real bearing on its ability to degrade these compounds to less toxic forms, or its use in bioremediation of materials contaminated with such compounds.

In contrast to RDX and HMX, which are easily broken down upon the initial reduction, nitroaromatic TNT is not well mineralized. Indeed, even though TNT was very quickly transformed (i.e. reduced) by *Methylobacterium* sp. BJ001, no significant release of $CO_2$ was recorded. For several decades, bacterial metabolism of nitroaromatic compounds has been known to lead to the formation of "dead-end" reduced derivatives not further transformed. Even though the reduction of nitro groups (electron withdrawing) into amino groups (electron donor) increases the reactivity of the aromatic ring, only very limited mineralization of TNT (less than 5.0%) has been observed in bacterial systems (29, 33). On the other hand, several reports have described a denitration of TNT with a release of nitrite ($NO_2$), which can be used by bacteria as a nitrogen source (6, 29, 56). However, the potential of *Methylobacterium* sp. BJ001 for fixing nitrogen prevents any conclusion about a possible utilization of TNT as a nitrogen source. Although bacterial transformation of TNT did not lead to a complete detoxification (i.e. mineralization), recalcitrant reduction metabolites are significantly less toxic than parent TNT (28) and may be bound to soil particles and humic acids, or conjugated to organic molecules, resulting in a reduction of bioavailability and toxicity (3).

Example 2

Taxonomic Analysis of $BJ001^T$

The bacterium isolated from poplar tissues, $BJ001^T$, was identified by phylogenetic analysis as a *Methylobacterium* sp. (FIG. 9). Members of the genus *Methylobacterium* are known to colonize the rhizosphere and the phyllosphere of a variety of plant species (60, 84, 64, 21, 51), although BJ001T is the first reported endophyte association with a poplar tree (*Populus* sp.). As discussed above, the isolate has characteristics of the *Methylobacterium* genus (13): Cells are rod-shaped (0.8–1.0×1.0–10.0 µm), frequently branched, occurring singly or in rosettes (FIGS. 11 and 12). They exhibit a polar growth and are motile by a single polar or lateral flagellum (see microphotographs of $BJ001^T$ in FIG. 13). Cells stained Gram-negative and colonies were pink to red. Cells are strictly aerobic and were tested catalase- and oxidase-positive (9). Due to the chemotaxonomic homogeneity of the genus *Methylobacterium*, phylogenic analyses constitute a critical tool for species identification (70, 66). According to 16S rDNA sequences, the closest relatives to $BJ001^T$ were *Methylobacterium thiocyanatum, Methylobacterium extorquens, Methylobacterium zatmanii*, and *Methylobacterium rhodesanium*, with 99.3, 99.1, 98.6, and 98.5% 16S sequence similarities respectively, which corresponds to the interspecies separation level of the genus *Methylobacterium* (94.2–99.4%; (67)). On the basis of 16S-23S IGS rDNA sequences, $BJ001^T$ shared 78.7–82.1% similarity with *M. extorquens* (The Genbank accession numbers of the 16S-23S IGS rDNA reference sequences are the following: *M. extorquens*, AF293375 and AF338180; *M. organophilum*, AF338181) and 66.5% with the type species, *M. organophilum*. The 16S and 16S-23S IGS rDNA sequence of $BJ001^T$ and the sequence similarity matrixes are shown in Tables 6 and 7. The levels of DNA relatedness between strain $BJ001^T$ and its close relatives as determined by DNA-DNA hybridization ranged from 15 to 59%, which allows the separation of $BJ001^T$ from the other members of the genus *Methylobacterium* (Table 5). Phenotypic differences between *Methylobacterium* species are limited and often rely on carbon- and energy-source utilization (68). Like the other members of the genus, $BJ001^T$ grew on $C_1$-substrates, such as methanol, methylamine, formate, and formaldehyde. In addition, BJ001$^T$ did use methane, an ability shared with only one other species of the genus, *M. organophilum* (78). BJ001$^T$ may play an important ecological role by consuming methane, whose greenhouse effect is 20 times more elevated than carbon dioxide (Trotsenko et al., 2001).

BJ001$^T$ differed from its closest relatives (i.e., *M. thiocyanate, M. extorquens, M. zatmanii*, and *M. rhodesianum*) by carbon-source utilization features summarized in Table 4: *M. thiocyanate* grows on glucose, arabinose, glutamate, citrate, and cyanate and thiocyanate, *M. zatmanii* grows on trimethylamine, and *M. rhodesianum* grows on dimethylamine, which did not support the growth of BJ001$^T$; on the other hand, *M. extorquens* does not use fructose, *M. zatmanii* does not use betaine, and *M. rhodesianum* does not use tartrate, which were all substrates for BJ001$^T$ (79, 83, 68, 58). Fructose, the first hexose synthesized by plant photosynthesis, is an optimal carbon substrate for BJ001$^T$. Carbon and nitrogen source utilization and enzymatic reactions of BJ001$^T$ are shown in Tables 7–9.

On the basis of 16S and 16S-23S IGS rDNA sequence similarities, DNA-DNA hybridization values, its carbon-source utilization pattern, including the use of methane, and its endophytic association with poplar trees, BJ001$^T$ is a novel *Methylobacterium* species, named herein *Methylobacterium populum* sp. nov.

Example 3

Description of *Methylobacterium populum* sp. nov.

*Methylobacterium populum* (po.pu.lum N. L. neut. adj. *Populum* of *Populus*, the Latin Name of Poplar).

The cells are aerobic, Gram-negative, asporogenous rods (0.8–1.0×1.0–10.0 μm) occurring singly, in pairs, or in rosettes. Cells are motile by one single polar or lateral flagella. Colonies are pink to red, slow growing, 0.1–0.2 mm in diameter after 4 days at 28° C. on LB or nutrient agar (NA) plates. The pink pigment is water-insoluble and has absorption maxima at 390, 473, 505, and 534 nm in a mixture of chloroform:methanol 1:1. The cells tested positive for the following enzymatic reactions: Catalase, oxidase, alkaline phosphatase, esterases ($C_4$ and $C_8$), valine arylamidase, α-chymotrypsine, acid phosphatase, and napthol-AS-BI-phosphohydrolase.

The cells utilized the following carbon-sources: D-fructose, glycerol, methanol, ethanol, formate, acetate, succinate, lactate, tartrate, pyruvate, fumarate, salicylate, formaldehyde, methylamine, methane, and betaine. Cells grow on LB and NA plates at 28° C. The cells do not use D- or L-arabinose, D-fucose, D-galactose, D-glucose, D-lactose, D-mannose, D-xylose, sucrose, iso-propanol, n-butanol, inositol, mannitol, sorbitol, L-aspartate, L-glutamate, glycine, citrate, sebacate, dimethylamine, trimethylamine, chloromethane, dichloromethane, cyanate or thiocyanate.

The utilized nitrogen-sources are ammonium, nitrate, L-alanine, L-aspartate, L-glutamate, L-glutamine, glycine, L-tryptophane, and methylamine.

The cellular fatty acids are hexadecanoate (palmitic acid, C16:0), 6.4±0.4% (n=3); cis-9-octadecenoate (oleic acid, C18:1$^9$), 81.6±2.1% (n=3); and octadecanoate (stearic acid, C18:0), 11.9±0.3% (n=3).

Optimal pH is 7.0. Cells do not grow at pH 4.0 or 9.0.

Optimal temperature is 20–30° C. Cells do not grow at 15 or 40° C.

Cells do not grow in the presence of 2.0% NaCl.

The G+C content is 70.4±0.3% (n=3). The GenBank accession number for the 16S and 16S-23S IGS rDNA sequence is AY251818.

The type strain, BJ001$^T$, was isolated from internal poplar tissues (*Populus deltoides×nigra* DN34) obtained from Hramoor Nursery (Manistee, Mich.) and has been deposited in the American Type Culture Collection as ATCC BAA-705$^T$ and at the National Collection of Industrial, Food, and Marine Bacteria as NCIMB 13946$^T$.

All chemicals used in the experiments described herein were of analytical grade and were purchased from Fluka (Ronkonkoma, N.Y.) or Sigma (St Louis, Mo.). Plant growth regulators and Phytagar were from Sigma. Phytagel was purchased from Gibco BRL (Rockville, Md.). $^{14}$C-[U-ring]-RDX and $^{14}$C-[U-ring]-HMX was purchased from DuPont NEN (Boston, Mass.) and exhibited an initial specific activity of 8.3 and 6.8 mCi mmol$^{-1}$ respectively. Both $^{14}$C-RDX and $^{14}$C-HMX were mixed with corresponding non-labeled compounds to obtain final specific activities of 4.5–9.1 and 3.0–1.6 nCi mmol$^{-1}$ for $^{14}$C-RDX and $^{14}$C-HMX respectively. 1$^4$C-[U-ring]-TNT was purchased from PerkinElmer Life Science (Boston, Mass.) and exhibited an initial activity of 40.0 mCi mmol$^{-1}$. $^{14}$C-TNT was mixed with non-labeled TNT to give a final specific activity of 2.1–3.3 nCi mmol$^{-1}$.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

REFERENCES

1. Ausubel, F. M., R. Brent, R. E. Kingston, D. D. Moore, J. G. Seidman, J. A. Smith, and K. Struhl. 1999. Short Protocols in Molecular Biology, 4th ed. John Wiley and Sons, New York, N.Y.
2. Binks, P. R., S. Nicklin, and N. C. Bruce. 1995. Degradation of Hexahydro-1,3,5-Trinitro-1,3,5-Triazine (Rdx) By *Stenotrophomonas-Maltophilia* Pbl. Appl. Environ. Microbiol. 61:1318–1322.
3. Bruns-Nagel, D., T. C. Schmidt, O. Drzyzga, E. von Low, and K. Steiubach. 1999. Identification of oxidized TNT metabolites in soil samples of a former ammunition plant. Environ. Sci. Pollut. Res. 6:7–10.
4. Coleman, N. V., D. R. Nelson, and T. Duxbury. 1998. Aerobic degradation of hexahydro-1,3,5-trinitro-1,3,5-triazine (RDX) as a nitrogen source by *Rhodococcus* sp. strain DN22. Soil Biol. Biochem. 30:1159–1167.
5. DeZwart, J. M., P. N. Nelisse, and J. G. Kuenen. 1996. Isolation and characterization of *Methylophaga sulfidovorans* sp.nov.: An obligate methylotrophic aerobic, dimethyl sulfide-oxidizing bacterium from a microbial mat. FEMS Microbiol. Ecol. 20:261–270.
6. Duque, E., A. Haidour, F. Godoy, and J. L. Ramos. 1993. Construction of a *Pseudomonas* hybrid strain that mineralizes 2,4,6-trinitrotoluene. J. Bacteriol. 175:2278–2283.
7. Etnier, E. L. 1989. Water quality criteria for hexahydro-1,3,5-trinitro-1,3,5-triazine (RDX). Regul. Toxicol. Pharmacolol. 9:147–157.
8. Fernando, T., J. A. Bumpus, and S. D. Aust. 1990. Biodegradation of TNT (2,4,6-trinitrotoluene) by *Phanerochaete chrysosporium*. Appl. Environ. Microbiol. 56:1666–1671.

9. Gerhardt, P., R. G. E. Murray, W. A. Wood, and N. R. Krieg. 1994. Methods for General and Molecular Bacteriology. American Society for Microbiology, Washington, D.C.
10. Gisi, D., L. Willi, H. Tarber, T. Leisinger, and S. Vuilleumier. 1998. Effects of bacterial host and dichloromethane dehalogenase on the competitiveness of methylotrophic bacteria growing with dichloromethane. Appl. Environ. Microbiol. 64:1194–1202.
11. Goodwin, K. D., R. K. Varner, P. M. Crill, and R. S. Oremland. 1995. Consumption of tropospheric levels of methyl bromide by $C_1$ compound-utilizing bacteria and comparison to saturation kinetics. Appl. Environ. Microbiol. 67:5437–5443.
12. Gorontzy, T., O. Drzyzga, M. W. Kahi, D. Bruns-Nagel, J. Breitung, E. von Loew, and K. H. Blotevogel. 1994. Microbial degradation of explosives and related compounds. Crit. Rev. Microbiol. 20:265–284.
13. Green, P. N. 1992. The genus *Methylobacterium*, p.2342–2349. In A. Balows, H. G. Truper, M. Dworkin, W. Harder, and K. H. Schleifer (ed.), The Prokaryotes, 2nd ed. Springer-Verlag, Berlin, Germany.
14. Hanson, R. S., and T. E. Hanson. 1996. Methanotrophic bacteria. Microbiol. Rev. 60:439–471.
15. Harkins, V. R., T. Mollhagen, C. Hientz, and K. Rainwater. 1999. Aerobic degradation of high explosives, phase I—HMX. Biorem. J. 3:285–290.
16. Hattwood, M. M., and W. Harder. 1972. A rapid and specific enrichment procedure for *Hyphomicrobium* spp. Antonie van Leeuwenhook 38:369–378.
17. Hawari, J. 2000. Biodegradation of RDX and HMX: From basic research to field application, p.277–310. In J. C. Spain, J. B. Hughes, and H. J. Knackmuss (ed.), Biodegradation of Nitroaromatic Compounds and Explosives, Lewis Publishers, New York, N.Y.
18. Hawari, J., S. Baudet, A. Halasz, S. Thiboutot, and G. Ampleman. 2000. Microbial degradation of explosives: Biotransformation versus mineralization. Appl. Microbiol. Biotechnol. 54:605–618.
19. Hiraishi, A., K Furuhata, A. Matsumoto, K. A. Koike, M. Fukuyama, and K. Tabuchi. 1995. Phenotypic and Genetic diversity of chlorine-resistant *Methylobacterium* strains isolates from various environments. Appl. Environ. Microbiol. 61:2099–2107.
20. Holland, M. A. 1997. Occam's razor applied to hormonology: Are cytokinin produced by plants? Plant. Physiol. 115:865–868.
21. Holland, M. A., and J. C. Polacco. 1994. PPFMs and other covert contaminats: Is there more to plant physiology than just plants? Annu. Rev. Plant Physiol. Plant Mol. Biol. 45:197–209.
22. Honeycutt, M. E., A. S. Jarvis, and V. A. McFarland. 1996. Cytotoxicity and mutagenicity of 2,4,6-trinitrotoluene and its metabolites. Ecotoxicol. Environ. Safety 35:282–287.
23. Ivanova, E. G., N. V. Doronina, and Y. A. Trotsenko. 2001. Facultative and obligate aerobic *Methylobacteria* synthesize cytokinins. Microbiology 70:452–458.
24. Jones, A. M., C. W. Greer, G. Ampleman, S. Thiboutot, J. Lavigne, and J. Hawari. 1995. Biodegradability of selected highly eneretic pollutants under aerobic conditions, p. 251–257. In R. Hinchee, R. B. Hoeppel, D. B. Anderson (ed.), 3rd Int. In Situ and On Site Bioreclam. Symposium, Battle Press, Colombus, Ohio.
25. Keith, L. H., and W. A. Telliard. 1979. Priority pollutants: A perspective view. Environ. Sci. Technol. 13:416–423.
26. Koening, R. L., R. O. Morris, and J. C. Polacco. 2002. tRNA is the source of low-level trans-zeatin production in *Methylobacterium* spp. J. Bacteriol. 184:1832–1842.
27. Kumar, S., K. Tamura, I. B. Jokobsen, and M. Nei. 2001. MEGA2: Molecular evolutionary genetics analysis software. Bioinformatics 17:1244–1245.
28. Lachance, B., P. Y. Robidoux, J. Hawari, G. Ampleman, S. Thiboutot, and G. I. Sunahara. 1999. Cytotoxic and genotoxic effects of energetic compounds on bacterial and mammalian cells in vitro. Mutat. Res. 444:25–39.
29. Lenke, H., C. Achtnich, and H. J. Knackmuss. 2000. Perspectives of bioelimination of polyaromatic compounds, p.91–126. In J. C. Spain, J. B. Hughes, and H. J. Knackniuss (ed.), Biodegradation of Nitroaromatic Compounds and Explosives, Lewis Publishers, New York, N.Y.
30. Lidstrom, M. E., and L. Chistoserdova. 2002. Plants in the Pink: Cytokinin production by *Methylobacterium*. J. Bacteriology 184:1818.
31. McCormick, N. G., J. H. Cornel, and A. M. Kaplan. 1981. Biodegradation of hexahydro-1,3,5-trinitro-1,3,5-triazine. Appl. Environ. Microbiol. 42:817–823.
32. Mo, K., C. O. Lora, A. E. Wanken, M. Javanmardian, X. Yang, and C. F. Kupla. 1997. Biodegradation of methyl t-buthyl ether by pure bacteria cultures. Appl. Environ. Microbiol. 47:69–72.
33. Nishino, S. F., J. C. Spain, and Z. He. 2000. Strategies for aerobic degradation of nitroaromatic compounds by bacteria: Process discovery to field application, p.7–61. In J. C. Spain, J. B. Hughes, and H. J. Knackmuss (ed.), Biodegradation of Nitroaromatic Compounds and Explosives, Lewis Publishers, New York, N.Y.
34. Pirtilla, A. M., H. Laukkanen, H. Pospiech, R. Myllyla, and A. Hohtola. 2000. Detection of intracellular bacteria in the buds of scotch pine (*Pinus sylvestris* L.) by in situ hybridization. Appl. Environ. Microbiol. 66:3073–3077.
35. Robidoux, P. Y., G. Bardai, L. Paquet, G. Ampleman, S. Thiboutot, J. Hawari, and G. I. Sunahara. 2003. Phytotoxicity of 2,4,6-trinitrotoluene (TNT) and octahydro-1,3,5,7-tetranitro-1,3,5,7-tetrazocine (HMX) in spiked artificial and natural forest soils. Arch. Environ. Contain. Tox. 44:198–209.
36. Robidoux, P. Y., C. Svendsen, J. Caumartin, J. Hawari, G. Ampleman, S. Thiboutot, J. M. Weeks, and G. I. Sunahara. 2000. Chronic toxicity of energetic compounds in soil determined using the earthworm (*Eisenia andrei*) reproduction test. Environ. Tox. Chem. 19:1764–1773.
37. Ross, R. H., and W. R. Hartley. 1990. Comparison of water quality criteria and health advisories for 2,4,6-trinitrotoluene (TNT). Regul. Toxicol. Pharmacol. 11:114–117.
38. Rosser, S. J., A. Basran, E. R. Travis, C. E. French, and N. C. Bruce. 2001. Microbial transformation of explosives. Adv. Appl. Microbiol. 49:1–35.
39. Sambrook, J., and D. W. Russel. 2001. Molecular Cloning: A Laboratory Manual. 3rd Ed. Spring Harbor Laboratory Press, New York, N.Y.
40. Schaefer, J. K., and R. S. Oremland. 1999. Oxidation of mathyl halides by the facultative methylotroph strain IMB-1. Appl. Environ. Microbiol. 65:5035–5041.
41. Schnoor, J. L., L. A. Licht, S. C. McCutcheon, N. L. Wolfe, and L. H. Carriera. 1995. Phytoremediation of organic and nutrient contaminants. Environ. Sci. Technol. 29:318A–323A.
42. Smock L. A., D. L. Stoneburner, and J. R. Clark. 1976. The toxic effects of trinitrotoluene (TNT) and its primary degradation products on two species of algae and the fathead minnow. Water. Res. 10:537–543. 43. Spain, J. C. 1995. Biodegradation of Nitroaromatic Compounds, Plenum Press, New York, N.Y.
44. Spain, J. C. 2000. Biodegradation of nitroaromatic compounds and explosives: Introduction, p. 1–6. In J. C. Spain, J. B. Hughes, and H. J. Knackmuss (ed.), Biodegradation of Nitroaromatic Compounds and Explosives, Lewis Publishers, New York, N.Y.
45. Spain, J. B., J. B. Hughes, and H. J. Knackmuss. 2000. Biodegradation of Nitroaromatic Compounds and Explosives, Lewis Publishers, New York, N.Y.
46. Sunahara, G. I., S. Dodard, M. Sarrazin, L. Paquet, J. Hawari, C. W. Greer, G. Ampleman, S. Thiboutot, and A. Y. Renoux. 1999. Ecological characterization of energetic substances using a soil extraction procedure. Ecotoxicol. Environ. Saf. 43:138–148.
47. Sy, A., E. Giraud, P. Jourand, N. Garcia, A. Willems, P. de Lajudie, Y. Prin, M. Neyra, M. Gills, C. Boivin-Masson, and B. Dreyfus. 2001. Methylotrophic *Methylobacterium* bacteria nodulate and fix nitrogen in symbiosis with legumes. J. Bacteriol. 183:214–220.
48. Talmage, S. S., D. M. Opresko, C. J. Maxwell, C. J. Welsh, F. M. Cretella, P. H. Reno, and F. B. Daniel. 1999. Nitroaromatic munition compounds: Environmental effects and screening values. Rev. Environ. Contam. Toxicol. 161:1–156.
49. Tan, Z., T. Blurek, P. Vinuesa, P. Muller, and J. K. Ladha. 2001. Specific detection of *Bradyrhizobium* and *Rhizobium* strains colonizing rice (*Oryza sativa*) roots by 16S-23S ribosomal DNA intergenic spacer-targeted PCR. Appl. Environ. Microbiol. 67:3655–3664.
50. Tourova, T. P., B. B. Kuznetsov, N. V. Doronina, and Y. A. Trotsenko. 2001. Phylogenic analysis of dechloromethane-utilizing aerobic methylotrophic bacteria. Microbiology 70:92–97.
51. Trotsenko, Y. A., E. G. Ivanova, and N. V. Doronina. 2001. Aerobic methylotrophic bacteria as phytosymbionts. Microbiology 70:725–736.
52. Trotsenko, Y. A., and N. V. Loginova. 1979. Pathways involved in the metabolism of methylated amines in bacteria. Usp. Mikrobiol. 14:28–55.
53. Van Aken, B., and S. N. Agathos. 2001. Biodegradation of nitrosubstituted explosives by white-rot fungi: A mechanistical approach, p 1–70. In A. I. Laskin, J. W. Bennett, and G. G. Gadd (ed.), Advances in Applied Microbiology, vol 48. Academic Press, New York, N.Y.
54. Van Aken, B., M. Hofrichter, K. Scheibner, A. I. Hatakka, H. Naveau, and S. N. Agathos. 1999. Transformation and mineralization of 2,4,6-trinitrotoluene (TNT) by manganese peroxidase from the white-rot basidiomycete *Phlebia radiata*. Biodegradation 10:83–91.
55. Van Aken, B., and J. L. Schnoor. 2002. Evidence of perchlorate ($ClO_4$) reduction in plant tissues (poplar tree) using radio-labeled $^{35}ClO_4$. Environ. Sci. Technol. 36:2789–2788.
56. Vorbeck, C., H. Lenke, P. Fischer, J. C. Spain, and H. J. Knackmuss. 1998. Initial reductive reactions in aerobic microbial metabolism of 2,4,6-trinitrotoluene. Appl. Environ. Microbiol. 64:246–252.
57. Won, W. D., L. H. DiSalvo, and J. Ng. 1976. Toxicity and mutagenicity of 2,4,6-trinitrotoluene and its microbial metabolites. Appl. Environ. Microbiol. 31:576–580.
58. Wood, A. P., P. K. Donovan, I. R. McDonald, S. L. Jordan, T. D. Morgan, S. Khan, J. Colin Murrel, and E. Borodina. 1998. A novel pink-pigmented facultative methylotroph, *Methylobacterium thiocyanatum* sp.nov., capable of growth on thiocyanate or cyanate as sole nitrogen source. Arch. Microbiol. 169:148–158.
59. Austin, B. & Goodfellow, M. (1979). *Pseudomonas mesophilica*: A new species of pink bacteria isolated from leaf surfaces. *Int J Syst Bacteriol* 29, 373–378.
60. Austin, B., Goodfellow, M., & Dickinson, C. H. (1978). Numerical taxonomy of phylloplane bacteria isolated from *Lolium perenne*. *J Gen Microbiol* 104, 139–155.
61. Bligh, E. G. & Dyer, W. J. (1959). A rapid method for total lipid extraction and purification. *Can J Biochem Physiol* 37, 911–917.
62. Bousfield, I. J. & Green, P. N. (1985). Reclassification of bacteria of the genus *Protomonas* Urakami and Komagata 1984 in the genus *Methylobacterium* (Patt, Cole, and Hanson) Emend. Green and Bousfield 1983. *Int J Syst Bacteriol* 35, 209.
63. Bozzola, J. J. & Russel, L. D. (1998). Electron Microscopy, 2nd ed. Jones & Bartlett Publishers, Sudbury, Miss.
64. Corpe, W. A. & Rheem, S. (1989). Ecology of the methylotrophic bacteria on living leaf surfaces. *FEMS Microbiol Ecol* 62, 243–249.
65. Denhardt, D. T. (1966). A membrane-filter technique for the detection of complementary DNA. *Biochem Biophys Res Com* 23, 641–646.
66. Doronina, N. V., Trotsenko, Y. A., Krausova, V. I., Boulygina, E. S. & Tourova, T. P. (2000). *Methylopila helvetica* sp. nov. and *Methylobacterium dichloromethanicum* sp. nov., novel aerobic facultatively methylotrophic bacteria utilizing dichloromethane. *Syst Appl Microbiol* 23, 210–218.
67. Doronina, N. V., Trotsenko, Y. A., Kuznetsov, B., Tourova, T. P. & Salkinoja-Salonen, M. S. (2002). *Methylobacterium suomiense* sp. nov. and *Methylobacterium lusitanum* sp. nov., aerobic, pink-pigmented, facultatively methylotrophic bacteria. *Int J Syst Evol Microbiol* 52, 773–776.
68. Green, P. N. (1992). The genus *Methylobacterium*, p. 2342–2349. In A. Balows, H. G. Truper, M. Dworkin, Harder W., and K. H. Schleifer (ed.), The Prokaryotes, 2nd ed. Springer-Verlag, Berlin, Germany.
69. Green, P. N. & Bousfield, I. J. (1983). Emendation of *Methylobacterium* Patt, Cole, and Hanson 1976; *Methylobacterium rhodinum* (Heuman 1962) comb. nov. corrig.; *Methylobacterium radiotolerans* (Ito and Iizuka 1971) comb. nov. corrig.; and *Methylobacterium mesophilicum* (Austin and Goodfellow 1979) comb. nov. *Int J Syst Bacteriol* 33, 875–877.
70. Green, P. N., Bousfield, I. J. & Hood, D. (1988). Three new *Methylobacterium* species: *M. rhodesanium* sp. nov., *M. zatmanii* sp. nov., and *M. fujisawaense* sp. nov. *Int J Syst Bacteriol* 38, 124–127.
71. Heuman, W. (1962). Die methodic der kreuzung stembildener bakterien. *Biol Zentralbl* 81, 341–354.
72. Hornei, B., Luneberg, E., Schmidt-Rotte, H., Maass, M., Weber, K., Heits, F., Frosch, M. & Solbach, W. (1999). Systemic infection of an immunocompromised patient with *Methylobacterium zatmanii*. *J Clin Microbiol* 37, 248–250.
73. Hurek, T., Wagner, B., & Reinhold-Hurek, B. (1997). Identification of N2-fixing plant- and fungus-associated *Azoarcus* species by PCR-based genomic fingerprints. *Appl Environ Microbiol* 63, 4331–4339.
74. Ito, H. & Iizuka, H. (1971). Taxonomic studies on a radioresistant *Pseudomonas*. XII. Studies of the microorganisms of cereal grain. *Agric Biol Chem* 35, 1566–1571.

75. Kouno, K. & Uzaki, A. (1975). Distribution of methanol-utilizing bacteria, p. 11–21. In Proceedings of the International Symposium on Microbial Growth on $C_1$ Compounds. Society of Fermentation Technology, Osaka, Japan.
76. McDonald, I. R., Doronina, N. V., Trotsenko, Y. A., McAnulla, C. & Murrell, J. C. (2001). *Hyphomicrobium chloromethanicum* sp. nov. and *Methylobacterium chloromethanicum* sp. nov., chloromethane-utilizing bacteria isolated from a polluted environment. *Int J Syst Evol Microbiol* 51, 119–122.
77. Mesbah, M., Premachandran, U. & Whitman, W. B. (1989). Precise measurement of the G+C content of deoxyribonucleic acid by high performance liquid chromatography. *Int J Syst Bacteriol* 39, 159–167.
78. Patt, T. E., Cole, G. C. & Hanson, R. S. (1976). *Methylobacterium*, a new genus of facultatively methylotrophic bacteria. *Int J Syst Bacteriol* 26, 226–229.
79. Rock, J. S., Goldberg, I., Ben-Bassat, A. & Mateles, R. I. (1976). Isolation and characterization of two methanol utilizing bacteria. *Agric Biol Chem* 40, 2129–2135.
80. Sy, A., Giraud, E., Jourand, P., Garcia, N., Willems, A., de Lajudie, P., Prin, Y., Neyra, M., Gillis, M., Boivin-Masson, C. & Dreyfus, B. (2001). Methylotrophic *Methylobacterium* bacteria nodulate and fix nitrogen in symbiosis with legumes. *J Bacteriol* 183, 214–220.
81. Truant, A. L., Gulati, R., Giger, O., Satishchandran, V., & Caya, J. G. (1998). *Methylobacterium* species: An increasingly important opportunistic pathogen. *Lab Med* 29, 704–710.
82. Urakami, T., Araki, H., Suzuki, K. & Komagata, K. (1993). Further studies of the genus *Methylobacterium* and description of *Methylobacterium aminovorans* sp. nov. *Int J Syst Bacteriol* 43, 504–513.
83. Urakami, T. & Komagata, K. (1984). *Protomonas*, a new genus of facultatively methylotrophic bacteria. *Int J Syst Bacteriol* 34, 188–201.
84. Yoshimura, F. (1982). Phylloplane bacteria in a pine forest. *Can J Microbiol* 28, 580–592.

TABLE 1

Mass Balance for $^{14}$C-TNT (25 mg L$^{-1}$), $^{14}$C-RDX (20 mg L$^{-1}$), and $^{14}$C-HMX (2.5 mg L$^{-1}$) treated by *Methylobacterium* sp. BJ001 growing in LB liquid medium after 55 days of exposure. Radioactivity is expressed as a percentage of the initial dose. Control experiments consisted in non-inoculated flasks.

| Radioactivity (%) | $^{14}$C-TNT (25 mg l$^{-1}$) | | $^{14}$C-RDX (20 mg l$^{-1}$) | | $^{14}$C-HMX (2.5 mg l$^{-1}$) | |
|---|---|---|---|---|---|---|
| | Cells | Control | Cells | Control | Cells | Control |
| Initial Solution | 100.0 ± 0.0 | 100.0 | 100.0 ± 0.0 | 100.0 ± 0.0 | 100.0 ± 0.0 | 100.0 |
| Final Solution | 93.3 ± 3.4 | 103.4 | 12.8 ± 1.5 | 104.4 | 12.5 ± 1.3 | 98.3 |
| Bacterial Cells | 6.3 ± 1.3 | 0.2 | 1.0 ± 0.2 | 0.0 | 0.9 ± 0.2 | 0.2 |
| Mineralization | 0.7 ± 0.4 | 0.6 | 58.0 ± 3.0 | 1.2 | 62.0 ± 3.9 | 1.1 |
| Mass Balance | 100.3 ± 4.7 | 104.2 | 71.8 ± 4.7 | 105.6 | 75.4 ± 5.4 | 99.6 |

TABLE 2

Mineralization of $^{14}$C-RDX (20 mg l$^{-1}$), $^{14}$C-HMX (2.5 mg l$^{-1}$), and $^{14}$C-TNT (25 mg l$^{-1}$) by *Methylobacterium* sp. BJ001 after 20 days of exposure. Cells were growing on minimal medium supplemented with the following carbon and/or nitrogen sources: Fructose (5.0 g l$^{-1}$) and $NH_4NO_3$ (1.2 g l$^{-1}$, 3.0 mM), fructose only, $NH_4NO_3$ only, and no fructose and no $NIH_4NO_3$. For each set of experiment, LB medium and non-inoculated minimal medium were used as positive and negative control media respectively. Control experiments consisted of the same set of media without addition of $^{14}$C-RDX, $^{14}$C-HMX, or $^{14}$C-TNT.

| Minimal Medium with | $^{14}CO_2$ (%) | Biomass (mg l$^{-1}$) | $^{14}CO_2$ (%) | Biomass (mg l$^{-1}$) |
|---|---|---|---|---|
| | $^{14}$C-RDX (20 mg l$^{-1}$) | | $^{14}$C-HMX (2.5 mg l$^{-1}$) | |
| Fructose and $NH_4NO_3$ | 7.74 ± 0.33 | 1.03 ± 0.11 | 6.75 ± 0.66 | 1.02 ± 0.22 |
| Fructose | 7.03 ± 0.91 | 0.74 ± 0.16 | 5.03 ± 0.32 | 1.07 ± 0.05 |
| $NH_4NO_3$ | 0.08 ± 0.03 | 0.11 ± 0.02 | 0.12 ± 0.08 | 0.09 ± 0.04 |
| No Fructose and no $NH_4NO_3$ | 0.19 ± 0.15 | 0.14 ± 0.08 | 0.18 ± 0.14 | 0.16 ± 0.06 |
| Control (+) LB | 18.08 ± 3.03 | 1.05 ± 0.07 | 15.54 ± 1.8 | 1.08 ± 0.06 |
| Control (−) | 0.35 ± 0.23 | 0.06 ± 0.02 | 0.11 ± 0.04 | 0.22 ± 0.24 |
| | $^{14}$C-TNT (25 mg l$^{-1}$) | | Control without $^{14}$C-RDX, $^{14}$C-HNX, or $^{14}$C-TNT | |
| Fructose and $NH_4NO_3$ | 0.34 ± 0.13 | 0.97 ± 0.06 | — | 1.06 ± 0.08 |
| Fructose | 0.25 ± 0.17 | 0.97 ± 0.13 | — | 1.08 ± 0.14 |
| $NH_4NO_3$ | 0.21 ± 0.10 | 0.16 ± 0.08 | — | 0.11 ± 0.03 |
| No Fructose or $NH_4NO_3$ | 0.19 ± 0.13 | 0.19 ± 0.05 | — | 0.17 ± 0.05 |

TABLE 2-continued

Mineralization of $^{14}$C-RDX (20 mg l$^{-1}$), $^{14}$C-HMX (2.5 mg l$^{-1}$), and $^{14}$C-TNT (25 mg l$^{-1}$) by *Methylobacterium* sp. BJ001 after 20 days of exposure. Cells were growing on minimal medium supplemented with the following carbon and/or nitrogen sources: Fructose (5.0 g l$^{-1}$) and NH$_4$NO$_3$ (1.2 g l$^{-1}$, 3.0 mM), fructose only, NH$_4$NO$_3$ only, and no fructose and no NH$_4$NO$_3$. For each set of experiment, LB medium and non-inoculated minimal medium were used as positive and negative control media respectively. Control experiments consisted of the same set of media without addition of $^{14}$C-RDX, $^{14}$C-HMX, or $^{14}$C-TNT.

| Minimal Medium with | $^{14}$CO$_2$ (%) | Biomass (mg l$^{-1}$) | $^{14}$CO$_2$ (%) | Biomass (mg l$^{-1}$) |
|---|---|---|---|---|
| Control (+) LB | 0.56 ± 0.07 | 1.06 ± 0.15 | — | 1.12 ± 0.07 |
| Control (−) | 0.35 ± 0.07 | 0.09 ± 0.06 | — | 0.09 ± 0.01 |

TABLE 3

Mineralization of $^{14}$C-RDX (20 mg l$^{-1}$), $^{14}$C-HMX (2.5 mg l$^{-1}$), and $^{14}$C-TNT (25 mg l$^{-1}$) by members of the genus *Methylobacterium* after 20 days of exposure. Cells were growing on LB medium supplemented with succinate (2.0 g l$^{-1}$). Control experiments were carried out with non-inoculated flasks.

| | $^{14}$CO$_2$ (%) | | |
|---|---|---|---|
| *Methylobacterium* Strain | $^{14}$C-RDX (20 mg l$^{-1}$) | $^{14}$C-HMX (2.5 mg l$^{-1}$) | $^{14}$C-TNT (25 mg l$^{-1}$) |
| M. extorquens | 15.2 ± 2.4 | 13.8 ± 1.9 | 0.2 ± 0.2 |
| M. organophilum | 8.4 ± 3.0 | 8.1 ± 0.7 | 0.4 ± 0.3 |
| M. rhodesianum | 13.7 ± 3.2 | 11.6 ± 2.0 | 0.3 ± 0.1 |
| BJ001 | 18.5 ± 1.7 | 17.2 ± 2.3 | 0.5 ± 0.3 |
| Control | 0.1 ± 0.0 | 0.6 ± 0.2 | 0.2 ± 0.0 |

| | Biomass (mg l$^{-1}$) | | |
|---|---|---|---|
| | $^{14}$C-RDX (20 mg l$^{-1}$) | $^{14}$C-HMX (2.5 mg l$^{-1}$) | $^{14}$C-TNT (25 mg l$^{-1}$) |
| M. extorquens | 1.01 ± 0.10 | 1.12 ± 0.06 | 1.07 ± 0.08 |
| M. organophilum | 1.23 ± 0.07 | 1.19 ± 0.10 | 1.13 ± 0.05 |
| M. rhodesianum | 0.95 ± 0.15 | 0.98 ± 0.08 | 1.00 ± 0.04 |
| BJ001 | 0.98 ± 0.11 | 0.99 ± 0.06 | 0.97 ± 0.05 |
| Control | 0.02 ± 0.01 | 0.02 ± 0.02 | 0.03 ± 0.07 |

TABLE 4

Differential carbon-substrate utilization among *Methylobacterium* species. Utilization of various compounds used as sole sources of carbon and energy are shown. Adapted from Green (13). See also Table 8.

| Organisms | BJ001$^T$ | M. amino-vorans[82] | M. chloro-methanicum[76] | M. ichloro-methanicum[66] | M. extorquens[83] | M. fujisawaense[75] | M. lusitanum[67] | M. mesophilicum[59] |
|---|---|---|---|---|---|---|---|---|
| D-Glucose | − | − | − | − | − | + | − | + |
| D-Fucose | − | ND | ND | ND | − | + | ND | + |
| D-Xylose | − | − | − | − | − | + | − | − |
| L-Arabinose | − | ND | ND | ND | − | + | − | + |
| D-Fructose | + | + | − | + | − | v | + | − |
| L-Aspartate/L-Glutamate | − | + | + | − | v | + | − | + |
| Citrate | − | − | + | + | − | + | − | + |
| Sebacate | − | ND | ND | ND | − | + | ND | v |
| Acetate | + | + | + | + | + | + | + | − |
| Betaine | + | + | + | + | + | − | − | − |
| Tartare | + | ND | ND | ND | v | v | − | − |
| Ethanol | + | ND | ND | ND | + | + | + | + |
| Methane | + | ND | − | − | − | − | − | − |
| Methylamine | + | + | + | + | + | − | + | − |
| Dimethylamine | − | + | ND | ND | − | − | − | − |
| Trimethyl-amine | − | + | − | − | − | − | − | − |
| Cyanate | − | ND | ND | ND | ND | ND | ND | ND |
| Thiocyanate | − | ND | ND | ND | ND | ND | ND | ND |
| Nutrient agar | + | ND | ND | ND | v | + | ND | − |

TABLE 4-continued

Differential carbon-substrate utilization among *Methylobacterium* species.
Utilization of various compounds used as sole sources of carbon and energy are shown.
Adapted from Green (13). See also Table 8.

| Organisms | *M. organophilum*[78] | *M. radiotolerans*[74] | *M. rhodesianum*[79] | *M. rhodinum*[71] | *M. suomiense*[67] | *M. thiocyanatum*[58] | *M. zatmanii*[79] |
|---|---|---|---|---|---|---|---|
| D-Glucose | + | + | – | w | + | + | – |
| D-Fucose | – | + | – | – | ND | ND | – |
| D-Xylose | – | + | – | – | – | ND | – |
| L-Arabinose | – | + | – | – | – | w | – |
| D-Fructose | + | – | + | + | + | + | + |
| L-Aspartate/L-Glutamate | – | + | v | + | – | + | – |
| Citrate | – | + | – | + | – | + | – |
| Sebacate | – | + | – | – | ND | ND | – |
| Acetate | + | + | + | + | + | + | + |
| Betaine | – | + | + | + | + | ND | – |
| Tartare | – | – | – | – | – | ND | v |
| Ethanol | + | v | + | + | + | ND | + |
| Methane | v | – | – | – | – | ND | – |
| Methylamine | + | – | + | + | + | + | + |
| Dimethylamine | – | – | + | – | – | – | – |
| Trimethylamine | + | – | – | – | – | – | + |
| Cyanate | ND | ND | ND | ND | ND | + | ND |
| Thiocyanate | ND | ND | ND | ND | ND | + | ND |
| Nutrient agar | + | + | + | + | ND | + | + |

+, Growth; –, no growth; v, variable; w, weak growth; ND, not determined

TABLE 5

DNA-DNA hybridization of *Methylobacterium* BJ001[T]
with the closest relatives. Hybridization procedure was
carried out according to the method of Denhardt (65)

| *Methylobacterium* Species | DNA-DNA Hybridization (%) |
|---|---|
| *Methylobacterium* BJ001[T] | 100 |
| *Methylobacterium thiocyanatum* DSM 11490 | 47 |
| *Methylobacterium extorquens* ATCC 14718 | 59 |
| *Methylobacterium zatmanii* JCM 2819 | 34 |
| *Methylobacterium rhodesanium* JCM 2810 | 25 |
| *Methylobacterium suomiense* VKM B-2238 | 33 |
| *Methylobacterium lusitanum* VKM B-2238 | 15 |
| *Methylobacterium organophilum* JCM 2833 | 28 |
| *Agrobacterium tumefasciens* NCPPB 2437 | 7 |

TABLE 6

16S rDNA sequence similarity matrix (%) for the genus *Methylobacterium*.
GenBank accession numbers are as follows: *Agrobacterium tumefasciens*, D14500;
BJ001[T], AY251818; *Escherichia coli*, J01859; *M. chloromethanicum*, AF198624; *M. dichloromethanicum*,
AF227128; *M. extorquens*, AF283375; *M. fujisawaense*, AJ250801;
*M. lusitanum*, AY009403; *M. mesophilicum*, AJ400919; *M. nodulans*, AF220763; *M. organophilum*,
D32226; *M. radiotolerans*, D32227; *M. rhodesianum*, D32228; *M. rhodinum*,
D32229; *M. suomicum*, AY009404; *M. zatmanii*, D32230;
*Rhodopseudomonas palustris*, D25312

| Organism | BJ001[T] | *M. thiocyanatum* | *M. extorquens* | *M. zatmanii* | *M. rhodesianum* | *M. suomiense* | *M. chloromethanicum* | *M. lusitanum* | *M. rhodinum* |
|---|---|---|---|---|---|---|---|---|---|
| BJ001[T] | 100 | 99.3 | 99.1 | 98.6 | 98.5 | 97.5 | 97.3 | 97.0 | 95.9 |
| *M. thiocyanatum* | — | 100 | 98.8 | 98.3 | 98.2 | 97.2 | 97.1 | 96.7 | 95.9 |
| *M. extorquens* | — | — | 100 | 99.0 | 98.8 | 97.5 | 98.2 | 96.8 | 96.2 |

TABLE 6-continued 16S rDNA sequence similarity matrix (%) for the genus *Methylobacterium*.
GenBank accession numbers are as follows: *Agrobacterium tumefasciens*, D14500;
BJ001[T], AY251818; *Escherichia coli*, J01859; *M. chloromethanicum*, AF198624; *M. dichloromethanicum*,
AF227128; *M. extorquens*, AF283375; *M. fujisawaense*, AJ250801;
*M. lusitanum*, AY009403; *M. mesophilicum*, AJ400919; *M. nodulans*, AF220763; *M. organophilum*,
D32226; *M. radiotolerans*, D32227; *M. rhodesianum*, D32228; *M. rhodinum*,
D32229; *M. suomicum*, AY009404; *M. zatmanii*, D32230;
*Rhodopseudomonas palustris*, D25312

| | | | | | | | | | |
|---|---|---|---|---|---|---|---|---|---|
| *M. zatmanii* | — | — | — | 100 | 98.2 | 97.0 | 97.2 | 96.1 | 95.8 |
| *M. rhodesianum* | — | — | — | — | 100 | 97.4 | 97.0 | 96.1 | 95.5 |
| *M. suomiense* | — | — | — | — | — | 100 | 95.8 | 95.8 | 95.4 |
| *M. chloromethanicum* | — | — | — | — | — | 13 | 100 | 95.0 | 94.6 |
| *M. lusitanum* | — | — | — | — | — | — | — | 100 | 94.2 |
| *M. rhodinum* | — | — | — | — | — | — | — | — | 100 |
| *M. organophilum* | — | — | — | — | — | — | — | — | — |
| *M. dichloromethanicum* | — | — | — | — | — | — | — | — | — |
| *M. fujisawaense* | — | — | — | — | — | — | — | — | — |
| *M. mesophilicum* | — | — | — | — | — | — | — | — | — |
| *M. nodulans* | — | — | — | — | — | — | — | — | — |
| *M. radiotolerans* | — | — | — | — | — | — | — | — | — |
| *R. palustris* | — | — | — | — | — | — | — | — | — |
| *A. tumefasciens* | — | — | — | — | — | — | — | — | — |
| *E. coli* | — | — | — | — | — | — | — | — | — |

| Organism | *M. organophilum* | *M. dichloromethanicum* | *M. fujisawaense* | *M. mesophilicum* | *M. nodulans* | *M. radiotolerans* | *R. palustris* | *A. tumefasciens* | *E. Coli* |
|---|---|---|---|---|---|---|---|---|---|
| BJ001[T] | 95.8 | 94.7 | 94.3 | 94.0 | 94.0 | 93.6 | 89.3 | 86.8 | 75.4 |
| *M. thiocyanatum* | 95.5 | 94.4 | 94.0 | 93.7 | 93.7 | 93.3 | 88.9 | 86.5 | 75.2 |
| *M. extorquens* | 96.4 | 95.0 | 94.3 | 94.3 | 94.1 | 93.9 | 89.1 | 86.8 | 75.4 |
| *M. zatmanii* | 95.5 | 94.4 | 93.9 | 93.7 | 93.6 | 93.3 | 88.6 | 86.8 | 75.2 |
| *M. rhodesianum* | 95.3 | 94.2 | 94.0 | 93.8 | 93.6 | 93.5 | 88.4 | 86.2 | 75.1 |
| *M. suomiense* | 95.2 | 94.1 | 93.9 | 93.5 | 93.1 | 93.3 | 88.4 | 86.4 | 74.9 |
| *M. chloro* | 94.6 | 93.3 | 92.7 | 92.5 | 92.3 | 92.3 | 87.6 | 85.3 | 74.0 |
| *M. lusitanum* | 94.2 | 92.8 | 92.2 | 92.6 | 92.5 | 91.8 | 87.9 | 85.1 | 74.3 |
| *M. rhodinum* | 94.6 | 92.9 | 93.8 | 93.4 | 92.4 | 93.2 | 88.3 | 86.2 | 74.1 |
| *M. organophilum* | 100 | 93.1 | 95.7 | 95.5 | 93.0 | 95.3 | 89.5 | 87.5 | 75.9 |
| *M. dichloromethanicum* | — | 100 | 92.6 | 91.7 | 91.3 | 92.5 | 87.3 | 84.8 | 74.3 |
| *M. fujisawaense* | — | — | 100 | 97.5 | 93.2 | 98.8 | 89.6 | 86.9 | 76.1 |
| *M. mesophilicum* | — | — | — | 100 | 93.6 | 97.1 | 89.8 | 86.4 | 76.4 |
| *M. nodulans* | — | — | — | — | 100 | 93.0 | 88.8 | 85.8 | 75.1 |
| *M. radiotolerans* | — | — | — | — | — | 100 | 89.6 | 86.5 | 75.8 |
| *R. palustris* | — | — | — | — | — | — | 100 | 87.1 | 75.2 |
| *A. tumefasciens* | — | — | — | — | — | — | — | 100 | 75.6 |
| *E. coli* | — | — | — | — | — | — | — | — | 100 |

TABLE 7

16S-23S IGS rDNA sequence similarity matrix (%) for members of the genus *Methylobacterium*. GenBank accession numbers are as follows: BJ001[T], AY251818; *M. extorquens*, AF283375 and AF338180 *M. organophilum*, AF338181

| Organisms | BJ001[T] | *M. extorquens* (AF338180) | *M. extorquens* (AF293375) | *M. organophilum* |
|---|---|---|---|---|
| BJ001[T] | 100 | 82.1 | 78.7 | 66.5 |
| *M. extorquens* (AF338180) | — | 100 | 84.6 | 64.6 |
| *M. extorquens* (AF293375) | — | — | 100 | 65.2 |
| *M. organophilum* | — | — | — | 100 |

TABLE 8

Carbon-substrate utilization by *Metylobacterium* sp. BJ001[T].
Experiments were carried out in mineral liquid medium supplemented with $NH_4NO_3$ (30 mM N) and various carbon sources (0.3–0.5% v/v or w/v) (69). Growth was monitored by the OD at 600 nm after 14 days incubation at 28 C.

| C-Source | Growth | C-Source | Growth |
|---|---|---|---|
| Control | 0 | Formate | + |
| D-Arabinose | 0 | Acetate | + |
| L-Arabinose | 0 | Propionate | + |
| D-Fructose | + | Succinate | + |
| D-Galactose | 0 | Oxalate | + |
| D-Glucose | 0 | Lactate | + |
| Glycerol | + | Citrate | 0 |
| D-Lactose | 0 | Tartrate | + |
| Saccharose | 0 | Salicylate | + |
| D-Mannose | 0 | Pyruvate | + |
| D-Xylose | 0 | Fumarate | + |
| D-Fucose | 0 | Sebacate | 0 |
| Methanol | + | Formaldehyde[a] | + |
| Ethanol | + | Methyamine | + |
| Iso-Propanol | 0 | Dimethylamine | 0 |
| n-Butanol | 0 | Trimethylamine | 0 |
| Inositol | 0 | Chloromethane | 0 |
| Mannitol | 0 | Dichloromethane | 0 |

TABLE 8-continued

Carbon-substrate utilization by *Metylobacterium* sp. BJ001[T]. Experiments were carried out in mineral liquid medium supplemented with $NH_4NO_3$ (30 mM N) and various carbon sources (0.3–0.5% v/v or w/v) (69). Growth was monitored by the OD at 600 nm after 14 days incubation at 28 C.

| C-Source | Growth | C-Source | Growth |
| --- | --- | --- | --- |
| Sorbitol | 0 | Methyl tert-Butyl Ether | 0 |
| L-Aspartate | 0 | Methane[b] | + |
| L-Glutamate | 0 | Nutrient Agar (NA)[c] | + |
| Betaine | 0 | Luria-Bertani (LB)[c] | + |

+, Growth;
0, no growth
[a]1.25 mM
[b]Atmosphere methane:oxygen 95:5, 90:10, and 80:10%
[c]Solid medium

TABLE 9

Nitrogen-substrate utilization by *Methylobacterium* sp. BJ001[T]. Experiments were carried out in mineral liquid medium supplemented with fructose (0.5% w/v) and various nitrogen sources (30 mM N) (69). Growth was monitored by the OD at 600 nm after 14 days incubation at 28° C.

| N-Source | Growth |
| --- | --- |
| Control | 0 |
| $NH_4Cl$ | + |
| $KNO_3$ | + |
| L-Alanine | + |
| L-Aspartate | + |
| L-Glutamate | + |
| L-Glutamine | + |
| Glycine | + |
| L-Tryptophane | + |
| Urea | + |
| Methylamine | + |

+, Growth;
0, no growth

TABLE 10

Phenotypic characterization of *Methylobacterim* sp. BJ001[T]. Dehydrated carbon-source utilization test based on a set of 49 organic compounds using API50CH System (Biomerieux, Montalieu-Verceiu, France) and biochemical (enzymatic reactions) test based on a set of 19 enzymatic assays using API ZYM system (Biomerieux)

| C-Source | +/− | C-Source | +/− | Enzymatic Reaction | +/− |
| --- | --- | --- | --- | --- | --- |
| Control | 0 | Arbutine | 0 | Control | 0 |
| Glycerol | + | Esculine | 0 | Alkaline Phosphatase | + |
| Erytritol | 0 | Saliciline | 0 | Esterase (C4) | + |
| D-Arabinose | 0 | Cellobiose | 0 | Esterase Lipase (C8) | + |
| L-Arabinose | 0 | Maltose | 0 | Lipase (C14) | 0 |
| Ribose | 0 | Lactose | 0 | Leucine Arylamidase | 0 |
| D-Xylose | 0 | Melibiose | 0 | Valine Arylamidase | + |
| L-Xylose | 0 | Saccharose | 0 | Cysteine Arylamidase | 0 |
| Adonitol | 0 | Trehalose | 0 | Trypsin | 0 |
| β-Methyl-Xyloside | 0 | Inuline | + | α-Chymotrypsin | + |
| | | Melezitose | 0 | Acid Phosphatase | + |
| Galactose | 0 | D-Raffinose | 0 | Naphtol-AS-BI-Phosphohydrolase | + |
| D-Glucose | 0 | Amidon | 0 | | |
| D-Fructose | + | Glycogene | 0 | α-Galactosidase | 0 |
| D-Mannose | 0 | Xylitol | 0 | β-Galactosidase | 0 |
| L-Sorbose | 0 | β-Gentiobiose | 0 | β-Glucuronase | 0 |
| Rhamnose | 0 | D-Turanose | 0 | α-Glucosidase | 0 |
| Dulcitol | 0 | D-Lyxose | 0 | β-Glucosidase | 0 |
| Inositol | 0 | D-Tagatose | 0 | N-Acetyl-β-Glucosaminidase | 0 |
| Mannitol | 0 | D-Fucose | 0 | | |
| Sorbitol | 0 | D-Arabitol | 0 | α-Mannosidase | 0 |
| α-Methyl-D-Mannoside | 0 | Gluconate | 0 | α-Fucosidase | 0 |
| | | 2-Keto-Gluconate | 0 | Oxidase[a] | + |
| α-Methyl-D-Glucoside | 0 | 5-Keto-Gluconate | 0 | Catalase[a] | + |
| N-Acetyl-Glucosamine | 0 | | | | |
| Amygdaline | 0 | | | | |

+, Growth/positive reaction; 0, no growth/negative reaction
[a]Carried out according to Gerhardt et al. (9)

The invention claimed is:

1. A method for degrading a nitroaromatic or nitramine compound to produce one or more degradation products, the method comprising contacting said compound with an isolated bacterium having all identifying characteristics of the *Methylobacterium* species strain BJ001 having ATCC Accession No. PTA-5125 and NCIMB Accession No. 13946, whereby one or more degradation products is produced.

2. The method of claim 1 wherein said compound is a high energy compound.

3. The method of claim 2 wherein said high energy compound is selected from the group consisting of TNT, RDX and HMX.

4. The method of claim 1 wherein the degradation products of said degrading have reduced toxicity relative to the toxicity of the nitroaromatic or nitramine compound degraded.

5. The method of claim 1 wherein said compound is substantially mineralized by said method.

6. The method of claim 1 wherein said contacting comprises distributing a composition comprising said bacterium to an environment in which one seeks to degrade a said compound.

7. The method of claim 6 wherein said composition comprising said bacterium is distributed over an area of soil, fresh water or sediment contaminated by a said compound.

8. The method of claim 1 wherein said contacting comprises combining a composition comprising said bacterium with soil, water or sediment obtained from a site contaminated with a said compound.

9. The method of claim 1 wherein said contacting comprises combining a preparation comprising an isolated bacterium having all identifying characteristics of the *Methylobacterium* species strain BJ001 having ATCC Accession No. PTA-5125 and NCIMB Accession No. 13946, with a sample comprising a said nitroaromatic or nitramine compound.

10. The method of claim 9 wherein said preparation further comprises one or more additional in microorganisms.

11. The method of claim 9 wherein said preparation further comprises one or more nutrients for said *Methylobacterium*.

12. The method of claim 9 wherein said sample is a soil sample.

13. The method of claim 12 further comprising the addition of one or more soil amendments to said soil sample.

14. The method of claim 13 wherein said one or more soil amendments comprises one or more of manure, wood chips, potato scraps, apple pomace and corncobs.

15. An isolated *Methylobacterium* having all identifying characteristics of the *Methylobacterium* species strain BJ001 having ATCC Accession No. PTA-5125 and NCIMB Aeccession No. 13946.

16. An isolated *Methylobacterium* which is the *Methylobacterium* having ATCC Accession No. PTA-5125 and NCIMB Accession No. 13946.

17. A method of preparing *Methylobacterium* species strain BJ001 comprising:
    inoculating a sterile preparation of growth medium that supports the growth of *Methylobacterium* species with a cell of *Methylobacterium* species strain BJ001 of ATCC Accession No. PTA-5125 and NCIMB Accession No. 13946 and
    incubating the preparation or growth medium to produce a preparation of said *Methylobacterium* species strain BJ001.

18. A composition comprising an isolated *Methylobacterium* having all identifying characteristics of the *Methylobacterium* species strain BJ001 having ATCC Accession No. PTA-5125 and NCIMB Accession No. 13946, and a high energy compound.

19. The composition of claim 18 wherein said high energy compound is one or mor TNT, RDX and HMX.

20. A composition comprising *Methylobacterium* species strain BJ001 having all identifying characteristics of ATCC Accession No. PTA-5125 and NCIMB Accession No. 13946 said composition having a cell concentration of at least 1% by volume of said *Methylobacterium*.

21. The composition of claim 20 having a cell concentration of 1% to 95% by volume.

22. A composition comprising
    an aqueous slurry of said material comprising a nitroaromatic or nitramine compound, and
    a *Methylobacterium* species having all identifying characteristics of *Methylobacterium* species strain BJ001 having ATCC Accession No. PTA-5125 and NCIMB Accession No. 13946,
    said aqueous slurry being 30% solid material (w/w).

23. The composition of claim 22 wherein said *Methylobacterium* species is present at a density of $10^9$ cells/ml or greater.

24. The composition of claim 22 having a pH in the range of pH 3.0 to pH 11.0.

25. The composition of claim 24, wherein the pH is in the range of pH 6.0 to pH 8.0.

26. The composition of claim 22 which is at a temperature of 4° C. to 41° C.

27. The composition of claim 22 which is at a temperature of 15° C. to 37° C.

28. The composition of claim 22 which is at an oxygen saturation or 5% to 100%.

29. The composition of claim 28 which is at an oxygen saturation of 20% to 100%.

30. A composition comprising a viable, dried *Methylobacterium* having all identifying characteristics of *Methylobacterium* species strain BJ001 having ATCC Accession No. PTA-5125 and NCIMB Accession No. 13946.

31. The composition of claim 30, further comprising an additional microbial species.

32. The composition of claim 31 wherein said additional microbial species is another member or the genus *Methylobacterium*.

33. The composition of claim 30, further comprising one or more nutrients for said *Methylobacterium*.

34. A kit for the degradation of a nitramine or nitroaromatic compound, the kit comprising a *Methylobacterium* having all identifying characteristics of the species having ATCC Accession No. PTA-5125 and NCIMB Accession No. 13946.

* * * * *

SEQUENCE LISTING

```
<160> NUMBER OF SEQ ID NOS: 1

<210> SEQ ID NO 1
<211> LENGTH: 2276
<212> TYPE: DNA
<213> ORGANISM: Methylobacterium sp.
<220> FEATURE:
<221> NAME/KEY: misc_feature
```

```
<222> LOCATION: (1)..(1477)
<223> OTHER INFORMATION: 16S rRNA gene sequence
<220> FEATURE:
<221> NAME/KEY: misc_feature
<222> LOCATION: (1478)..(2110)
<223> OTHER INFORMATION: 16S-23S Intergenic Spacer
<220> FEATURE:
<221> NAME/KEY: misc_feature
<222> LOCATION: (2111)..(2276)
<223> OTHER INFORMATION: 23S rRNA gene

<400> SEQUENCE: 1
```

| | | | | | |
|---|---|---|---|---|---|
| agggtttgat | cctggctcag | agcgaacgct | ggcggcaggc | ttaacacatg | caagtcgaac    60 |
| gggcttcttc | ggaagtcagt | ggcagacggg | tgagtaacac | gtgggaacgt | gcccttcggt   120 |
| tcggaataac | tcagggaaac | ttgagctaat | accggatacg | cccttacggg | gaaaggttta   180 |
| ctgccgaagg | atcggcccgc | gtctgattag | cttgttggtg | gggtaacggc | ctaccaaggc   240 |
| gacgatcagt | agctggtctg | agaggatgat | cagccacact | gggactgaga | cacggcccag   300 |
| actcctacgg | gaggcagcag | tggggaatat | tggacaatgg | gcgcaagcct | gatccagcca   360 |
| tgccgcgtga | gtgatgaagg | ccttagggtt | gtaaagctct | tttgtccggg | acgataatga   420 |
| cggtaccgga | agaataagcc | ccggctaact | tcgtgccagc | agccgcggta | atacgaaggg   480 |
| ggctagcgtt | gctcggaatc | actgggcgta | aagggcgcgt | aggcggccga | ttaagtcggg   540 |
| ggtgaaagcc | tgtggctcaa | ccacagaatt | gccttcgata | ctggttggct | tgagaccgga   600 |
| agaggacagc | ggaactgcga | gtgtagaggt | gaaattcgta | gatattcgca | agaacaccag   660 |
| tggcgaaggc | ggctgtctgg | tccggttctg | acgctgaggc | gcgaaagcgt | ggggagcaaa   720 |
| caggattaga | taccctggta | gtccacgccg | taaacgatga | atgccagccg | ttggcctgct   780 |
| tgcaggtcag | tggcgccgct | aacgcattaa | gcattccgcc | tggggagtac | ggtcgcaaga   840 |
| ttaaaactca | aaggaattga | cgggggcccg | cacaagcggt | ggagcatgtg | gtttaattcg   900 |
| aagcaacacg | cagaacctta | ccatcccttg | acatggcatg | ttacctcgag | agatcgggga   960 |
| tcctcttcgg | aggcgtgcac | acaggtgctg | catggctgtc | gtcagctcgt | gtcgtgagat  1020 |
| gttgggttaa | gtcccgcaac | gagcgcaacc | cacgtcctta | gttgccatca | ttcagttggg  1080 |
| cactctaggg | agactgccgg | tgataagccg | cgaggaaggt | gtggatgacg | tcaagtcctc  1140 |
| atggccctta | cgggatgggc | tacacacgtg | ctacaatggc | ggtgacagtg | ggacgcgaaa  1200 |
| ccgcgaggtt | gagcaaatcc | ccaaaagccg | tctcagttcg | gattgcactc | tgcaactcgg  1260 |
| gtgcatgaag | gcggaatcgc | tagtaatcgt | ggatcagcac | gccacggtga | atacgttccc  1320 |
| gggccttgta | cacaccgccc | gtcacaccat | gggagttggt | cttacccgac | ggcgctgcgc  1380 |
| caaccgcaag | gggcaggcg | accacggtag | ggtcagcgac | tggggtgaag | tcgtaacaag  1440 |
| gtagccgtag | gggaacctgc | ggctggatca | cctcctttct | aaggatgttt | cttttgggag  1500 |
| tttggctccg | gccgatctgc | tactcgagac | gtcattggat | acatgaagcc | cagtcagggc  1560 |
| ttcgattggc | gggacctgga | gaggccgccc | tcgtttctct | ttctcatccg | gataagcggg  1620 |
| atcgctggac | gcgcgttgc | gtgatgcaac | ggctgtcgat | cggcgaccg | gctgggcct  1680 |
| gtagctcagg | tggttagagc | gcacccctga | taagggtgag | gtcggacgtt | cgagtcgtcc  1740 |
| caggcccacc | atgatcaggg | gacgtagctc | agctgggaga | gcagttgctt | tgcaagcatc  1800 |
| aggtcgtcgg | ttcgatcccg | tccgtctcca | ccagcgcttc | ttcgtgaggc | gcggtcgtat  1860 |
| ccggagagag | agtgcaagtt | tgcccttgtg | agtgctgagc | gccgcaggcg | gcattgatat  1920 |
| cgaacatcgt | gaagagggaa | tgtggccgca | ggttccgcga | aagcgggtcg | cctgttgcag  1980 |

```
gtcatgttcg gcaagcatgt gatgcgggtt ccgagaggag cctgcatcac tggtctttat    2040
cgtgaccgtg gctgggtgat cggcagcagc ttagctgctg cggatcacac cggacatcga    2100
tcatgagagc gatcaagtgc cttaagagca ttcggtggat gccttggcgc tgagaggcga    2160
tgaaggacgt ggtacgctgc gataagcctt ggggagctgc gaacgagctt tgatccaggg    2220
atttccgaat ggggcaaccc ggaatcgaat tcccgcggcc gccatggcgg ccggga        2276
```